United States Patent [19]
Catt et al.

[11] Patent Number: 5,981,571
[45] Date of Patent: Nov. 9, 1999

[54] BENZODIOXA ALKYLENE ETHERS AS MELATONERGIC AGENTS

[75] Inventors: John D. Catt, Southington; Graham Johnson, Madison; Daniel J. Keavy, Killingworth; Ronald J. Mattson, Meriden; Michael F. Parker; Katherine S. Takaki, both of Middletown; Joseph P. Yevich, Southington, all of Conn.

[73] Assignee: Bristol-Myers Squibb Company, Princeton, N.J.

[21] Appl. No.: 09/169,784

[22] Filed: Oct. 9, 1998

Related U.S. Application Data

[62] Division of application No. 08/987,478, Dec. 9, 1997, Pat. No. 5,856,529
[60] Provisional application No. 60/032,689, Dec. 10, 1996.

[51] Int. Cl.$^6$ ............ C07D 317/60; C07D 319/08; A61K 31/36; A61K 31/35
[52] U.S. Cl. ............ 514/450; 514/452; 514/466; 549/350; 549/362; 549/441
[58] Field of Search ................ 549/350, 362, 549/441; 514/450, 452, 466

[56] References Cited

U.S. PATENT DOCUMENTS 5,596,019  1/1997  Mattson et al. .................. 514/269

FOREIGN PATENT DOCUMENTS

| 48729/93 | 10/1993 | Australia . |
|---|---|---|
| 420 064 | 4/1991 | European Pat. Off. . |
| 447 285 | 9/1991 | European Pat. Off. . |
| 506 539 | 9/1992 | European Pat. Off. . |
| 527 687 | 2/1993 | European Pat. Off. . |
| 530 087 | 3/1993 | European Pat. Off. . |
| 562 956 | 9/1993 | European Pat. Off. . |
| 708 099 | 10/1994 | European Pat. Off. . |
| 747 346 | 12/1996 | European Pat. Off. . |
| WO 94/07487 | 4/1994 | WIPO . |
| WO 95/17405 | 6/1995 | WIPO . |
| WO 95/29173 | 11/1995 | WIPO . |

OTHER PUBLICATIONS

Arendt, J., et al., "Alleviation of Jet Lag by Melatonin: Preliminary Results of Controlled Double Blind Trial", *Br. Med. J.*, 292, pp. 1170–1172 (May 1986).

Cassone, V.M., et al., "Dose–Dependent Entrainment of Rat Circadian Rhythms by Daily Injection of Melatonin", *J. Biol. Rhythms*, 1, (3), pp. 219–229 (1986).

Copinga, S., et al., "2–Amino–8–methoxytetralins: A Series of Nonindolic Melatonin–like Agents", *J. Med. Chem.*, 36, pp. 2891–2898 (1993).

Reppert, S.M., et al., "Cloning and Characterization of a Mammalian Melatonin Receptor That Mediates Reproductive and Circadian Responses", *Neuron*, 13, pp. 1177–1185 (Nov. 1994).

Reppert, S.M., et al., "Molecular Characterization of a Second Melatonin Receptor Expressed in Human Retina and Brain: The Mel$_{1b}$ Melatonin Receptor", *Proc. Natl. Acad. Sci. USA*, 92, pp. 8734–8738 (Sep. 1995).

*Primary Examiner*—Bernard Dentz
*Attorney, Agent, or Firm*—Aldo A. Algieri

[57] ABSTRACT

Novel derivatives of benzodioxa alkylene ethers are provided which are useful as melatonergic agents.

11 Claims, No Drawings

BENZODIOXA ALKYLENE ETHERS AS MELATONERGIC AGENTS

CROSS-REFERENCE TO RELATED APPLICATION

This is a divisional application of application U.S. Ser. No. 08/987,478 filed Dec. 9, 1997 now U.S. Pat. No. 5,856,529, which claims the benefit of provisional application, U.S. Ser. No. 60/032,689 filed Dec. 10, 1996.

BACKGROUND OF THE INVENTION

The invention pertains to novel substituted benzodioxoles, benzofurans, dihydrobenzofurans, benzodioxanes and related derivatives having drug and bio-affecting properties and to their preparation, pharmaceutical formulations and use. In particular, the invention concerns benzodioxoles, benzofurans, dihydrobenzofurans and related derivatives bearing substituted amino methyl cyclopropyl groups. These compounds possess melatonergic properties that should make them useful in treating certain medical disorders.

Melatonin (N-acetyl-5-methoxytryptamine) is a hormone which is synthesized and secreted primarily by the pineal gland. Melatonin levels show a cyclical, circadian pattern with highest levels occurring during the dark period of a circadian light-dark cycle. Melatonin is involved in the transduction of photoperiodic information and appears to modulate a variety of neural and endocrine functions in vertebrates, including the regulation of reproduction, body weight and metabolism in photoperiodic mammals, the control of circadian rhythms and the modulation of retinal physiology.

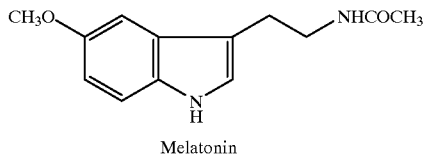

Melatonin

Recent evidence demonstrates that melatonin exerts its biological effects through specific receptors. Use of the biologically active, radiolabelled agonist [$^{125}$I]-2-iodomelatonin has led to the identification of high affinity melatonin receptors in the CNS of a variety of species. The sequences of two cloned human melatonin receptors have been reported [Reppert, et al., *Proc. Natl. Acad. Sci.* 92, p. 8734–8738, (1995) and Reppert, et al., *Neuron* 13, p. 1177–1185, (1994)]. In mammalian brain, autoradiographic studies have localized the distribution of melatonin receptors to a few specific structures. Although there are significant differences in melatonin receptor distribution even between closely related species, in general the highest binding site density occurs in discreet nuclei of the hypothalamus. In humans, specific [$^{125}$I]-2-iodomelatonin binding within the hypothalamus is completely localized to the suprachiasmatic nucleus, strongly suggesting the melatonin receptors are located within the human biological clock.

Exogenous melatonin administration has been found to synchronize circadian rhythms in rats (Cassone, et al., *J. Biol. Rhythms,* 1:219–229, 1986). In humans, administration of melatonin has been used to treat jet-lag related sleep disturbances, considered to be caused by desynchronization of circadian rhythms (Arendt, et al., *Br. Med. J.* 292:1170, 1986). Further, the use of a single dose of melatonin to induce sleep in humans has been claimed by Wurtman in International Patent Application WO 94/07487, published on Apr. 14, 1994.

Thus, melatonin agonists should be particularly useful for the treatment of sleep disorders and other chronobiological disorders. Melatonin agonists would also be useful for the further study of melatonin receptor interactions as well as in the treatment of conditions affected by melatonin activity, such as depression, jet-lag, work-shift syndrome, sleep disorders, glaucoma, reproduction, cancer, premenstrual syndrome, immune disorders, inflammatory articular diseases and neuroendocrine disorders.

Aside from simple indole derivatives of melatonin itself, various bicyclic structures have been prepared and their use as melatonin ligands disclosed. In general these bicyclic amide structures can be represented as:

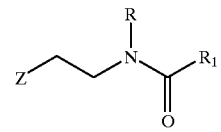

wherein Z is an aryl or heteroaryl system attached by a two carbon bridge to the amide group. Some specific examples follow.

Yous, et al. in European Patent Application EP-527,687A, published on Feb.17, 1993, disclose as melatonin ligands arylethylamines i,

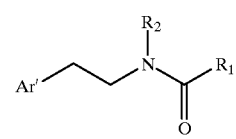

wherein Ar' is, inter alia, a substituted or unsubstituted benzo[b]thiophen-3-yl, benzimidazol-1-yl, benzo[b]furan-3-yl, 1,2-benzisoxazol-3-yl, 1,2-benzisothiazol-3-yl, or indazol-3-yl radical; $R_1$ is, inter alia, an alkyl or cycloalkyl group; and $R_2$ is hydrogen or lower alkyl.

Yous, et al. in European Patent Application EP-506,539A, published on Sep. 30, 1992, claim ligands ii,

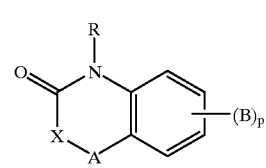

wherein A is oxygen or sulfur; X is a methylene group or a bond; and R is H or lower alkyl when p is 1 and B is defined by the radical iii,

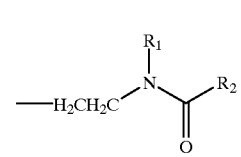

wherein $R_1$ is hydrogen or lower alkyl and $R_2$ is inter alia, hydrogen, lower alkyl or cycloalkyl. Alternatively, R is defined by the radical iii when p is 0 or 1 and B is lower alkoxy.

Several naphthalene derivatives have also been disclosed as melatonin ligands.

Andrieux, et al. in European Patent Application EP-447,285A, published on Sep. 18, 1991, claim amidoalkylnaphthalenes iv,

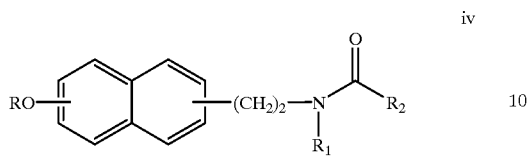

wherein R is lower alkyl; $R_1$ is hydrogen or lower alkyl; and $R_2$ is, inter alia, hydrogen, lower alkyl, or cycloalkyl.

Yous, et al. in European Patent Application EP-562,956A, published on Sep. 29, 1993, disclose amide and urea naphthalene derivatives v,

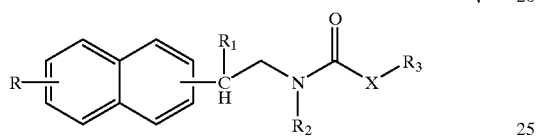

in which R is hydrogen or $OR_4$ wherein $R_4$ is, inter alia, hydrogen, alkyl, cycloalkyl, or cycloalkylalkyl; $R_1$ is hydrogen or $COOR_5$ wherein $R_5$ is hydrogen or alkyl; $R_2$ is hydrogen or alkyl; X is NH or a bond; and $R_3$ is, inter alia, alkyl, alkenyl, or cycloalkyl.

Lesieur, et al. in European Patent Application EP-530,087A, published on Mar. 3, 1993, disclose naphthylethylureas and naphthylethylthioureas vi,

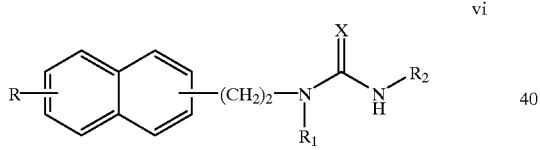

in which R is hydrogen or $OR_3$ wherein $R_3$ is, inter alia, hydrogen, lower alkyl, or cycloalkyl; $R_1$ is hydrogen or lower alky; X is oxygen or sulfur; and $R_2$ is, inter alia, lower alkyl or cycloalkyl.

Langlois, et al., in Australian Patent Application AU-A-48729/93 disclose arylalkyl(thio)amides vii as melatonergic ligands,

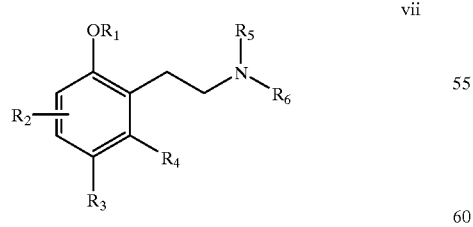

wherein $R_1$ is hydrogen or lower alkyl; $R_2$ is hydrogen, halogen, or lower alkyl; $R_3$ and $R_4$ are identical or different groups including, inter alia, hydrogen, halogen, or lower alkyl or $R_3$ and $R_4$, together with the benzene ring which carries them, form a ring-system $E_3$ chosen from, inter alia, naphthalene, on the understanding that the portion of the ring-system $E_3$ formed by $R_3$ and $R_4$ and the two carbon atoms of the benzene ring which carry them is unhydrogenated or partially hydrogenated; $R_5$ is hydrogen or lower alkyl; and $R_6$ is,

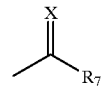

wherein X is sulfur or oxygen and $R_7$ is, inter alia, lower alkyl or alkenyl. Compound viii is included as a specific example,

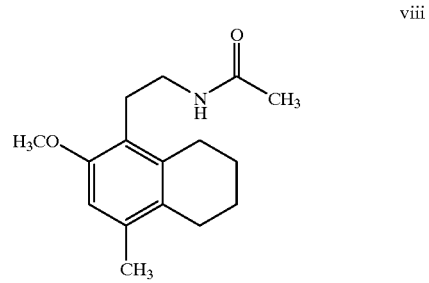

Horn and Dubocovich in European Patent Application EP-420,064A, published on Apr. 3, 1991, disclose 2-amidotetralins ix as melatonin ligands,

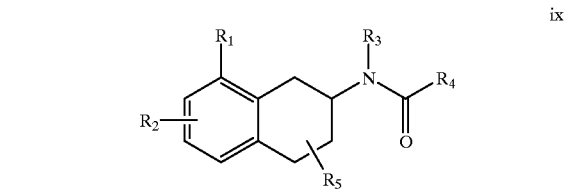

wherein $R_1$ is, inter alia, hydrogen, lower alkyl, or lower alkoxyl; $R_2$ is, inter alia, hydrogen, halogen, or lower alkoxyl; $R_3$ is, inter alia, hydrogen, or lower alkyl; $R_4$ is, inter alia, lower alkyl, haloalkyl or cycloalkyl; and $R_5$ is hydrogen, hydroxyl, halogen, oxo, aryl, lower alkyl or alkylaryl.

Copinga et al, in *J. Med. Chem.*, 36, p. 2891–2898 (1993), discusses amidomethoxytetralins of structure x and their melatonergic properties.

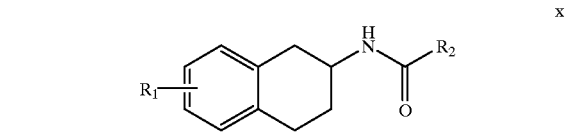

In structure x, $R_1$ is H or $OCH_3$ and $R_2$ is alkyl, haloalkyl, phenylalkyl or phenyl.

Lesieur et al, in EP-708,099A, published Apr. 24, 1996, disclose compounds of structure xi, which are useful for the treatment of diseases caused by a melatonin imbalance.

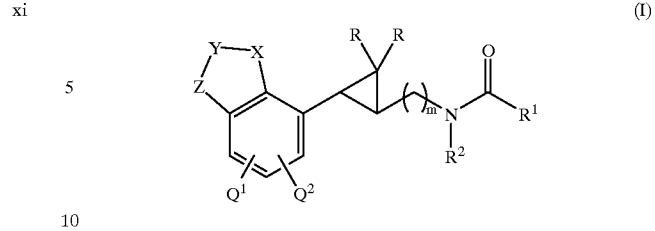

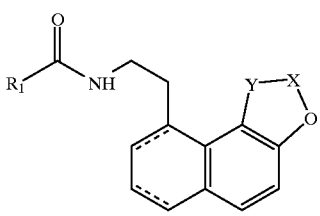

wherein - - - is a single or double bond; $R_1$=Me or MeNH; and X—Y=—CH(Me)—CH$_2$—, CH$_2$CH(OH)— or (CH$_2$)$_3$—.

North et al., in International Application WO 95/29173, published Nov. 2, 1995, disclose naphthalene derivatives of structure xii:

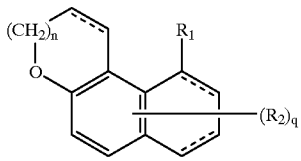

wherein $R_1$ is a group of the formula $CR_3R_4(CH_2)_p NR_5COR_6$; $R_2$ is hydrogen, halogen, $C_{1-6}$ alkyl, $OR_7$ or $CO_2R_7$; and may be the same or different substituent when q is 2; $R_3$, $R_4$ and $R_5$, which may be the same or different, are hydrogen or $C_{1-6}$ alkyl; $R_6$ is $C_{1-6}$ alkyl or $C_{3-7}$ cycloalkyl; $R_7$ is hydrogen or $C_{1-6}$ alkyl; n is zero, 1 or 2; p is an integer of 1, 2, 3 or 4; q is 1 or 2; and the dotted lines indicate the absence or presence of an additional bond. The North et al. compounds are taught to treat chronobiological disorders.

In International Application WO 95/17405, published on Jun. 29, 1995, North et al., disclose compounds of structure xiii and teach their use in the treatment of conditions related to the melatonin system.

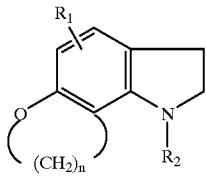

wherein $R_1$ is hydrogen, halogen or $C_{1-6}$ alkyl; $R_2$ is a group of formula —$CR_3R_4(CH_2)_pNR_5COR_6$; $R_3$, $R_4$ and $R_5$, which may be the same or different, are hydrogen or $C_{1-6}$ alkyl; $R_6$ is $C_{1-6}$ alkyl or $C_{3-7}$ cycloalkyl; n is an integer of 2, 3 or 4; and p is an integer of 1, 2, 3 or 4.

The foregoing disclosures do not teach or suggest the novel melatonergic benzodioxole, benzofuran or dihydrobenzofurans of the present invention. The novel compounds of the present invention display melatonergic agonist activity.

SUMMARY OF THE INVENTION

The invention provides a novel series of compounds of Formula I wherein R, $R^1$, $R^2$, $Q^1$, $Q^2$, X, Y, Z and m are as defined below, including hydrates and solvates thereof which bind to human melatonergic receptors and therefore are useful as melatonergic agents in the treatment of sleep disorders, seasonal depression, shifts in circadian cycles, melancholia, stress, appetite regulation, benign prostatic hyperplasia and related conditions.

DETAILED DESCRIPTION OF THE INVENTION

The invention provides a novel series of compounds of Formula I and solvates thereof having the formula:

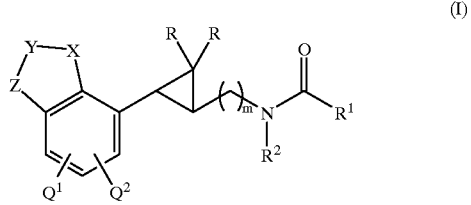

wherein $Q^1$ and $Q^2$ each are independently hydrogen or halogen;
X is CH$_2$, CH or oxygen;
Y is $CR^3$, $CR^3R^4$ or $(CH_2)_n$, with n=1–4;
Z is CH$_2$, CH or oxygen;
R is hydrogen, halogen or $C_{1-4}$ alkyl in both cases;
m is 1 or 2;
$R^1$ is $C_{1-6}$ alkyl, $C_{3-6}$ cycloalkyl, $C_{1-3}$ haloalkyl, $C_{1-6}$ alkylamino, $C_{2-6}$ alkenyl, $C_{1-4}$ alkoxy($C_{1-4}$)alkyl, $C_{1-4}$ alkylthio($C_{1-4}$)alkyl or $C_{1-4}$ trifluoromethylalkyl;
$R^2$ is hydrogen or $C_{1-4}$ alkyl; and
$R^3$ and $R^4$ each are independently hydrogen or $C_{1-4}$ alkyl.

The present invention also provides a method for the treatment of sleep disorders and related conditions, which comprises administering a therapeutically effective amount of a compound of Formula I or a solvate or hydrate thereof.

$Q^1$ and $Q^2$ are selected from H and halogen (i.e., bromine, chlorine, iodine or fluorine). It is most preferred that $Q^1$ and $Q^2$ be H.

X may be CH$_2$, CH (when a double bond is present) or oxygen.

Y is $CR^3$ (when a double bond is present), $CR^3R^4$ or —(CH$_2$)n— and n is 1 through 4, but is preferably 1 or 2.

Z may be CH$_2$, CH (when a double bond is present) or oxygen, with oxygen being most preferred.

When X and Y are CH$_2$ and Z is oxygen or Z and Y are CH$_2$ and X is oxygen, the compound is a dihydrobenzofuran. When X and Y are CH and Z is oxygen or Z and Y are CH and X is oxygen, the compound is a benzofuran. When X and Z are oxygen and Y is CH$_2$, the compound is a benzodioxole. When X and Z are oxygen and Y is (CH$_2$)$_2$, the compound is benzodioxane. Compounds in which X and Y are CH$_2$ and Z is oxygen are preferred.

Both R groups are the same moiety. Useful R groups include hydrogen, halogen and $C_{1-4}$ alkyl. R is preferably hydrogen.

m is 1 or 2, with m=1 preferred.

$R^1$ is one of several types of groups. $R^1$ is selected from is $C_{1-6}$ alkyl, $C_{3-6}$ cycloalkyl, $C_{1-3}$ haloalkyl, $C_{1-6}$ alkylamino, $C_{2-6}$ alkenyl, $C_{1-4}$ alkoxy($C_{1-4}$)alkyl, $C_{1-4}$ alkylthio($C_{1-4}$)alkyl or $C_{1-4}$ trifluoromethylalkyl. $R^1$ is preferably $C_{1-6}$ alkyl or $C_{3-6}$ cycloalkyl.

$R^2$ is hydrogen or $C_{1-4}$ alkyl. $R^2$ is preferably hydrogen.

$R^3$ and $R^4$ are hydrogen or $C_{1-4}$ alkyl. It is preferred that $R^3$ and $R^4$ both be hydrogen. It is also preferred that $R^3$ is hydrogen and $R^4$ is methyl. When $R^3$ is hydrogen and $R^4$ is methyl, both enantiomers and racemate are preferred.

"Alkyl" means a monovalent straight or branched chain group of the formula $C_xH_{2x+1}$, with x being the number of carbon atoms.

"Y—X" and "Y—Z" refer to a single bond or double bond attachment when defined by the substituents X, Y, and Z.

"Cycloalkyl" groups are monovalent cyclic moieties containing at least 3 carbon atoms and conforming to the formula $C_xH_{(2x-1)}$, with x being the number of carbon atoms present. The cyclopropyl group is a preferred cycloalkyl moiety.

"Haloalkyl" includes straight and branched chain hydrocarbon radicals bearing from 1 to 3 halogen moieties. "Halogen" means F, Cl, Br or I. Preferred halogens in haloalkyl moieties of $R_1$ include F and Cl.

"Alkylamino" refers to —NH-alkyl substituents containing 1 to 6 carbon atoms, preferably —NHCH$_3$ or —NHCH$_2$CH$_3$ groups.

Preferred compounds have IC$_{50}$ values of 250 nM or less in melatonergic binding tests described herein.

One group of preferred compounds include the benzofurans of Formula I wherein the group, —X—Y—Z—, consists of —CH=CH—O— and —CH=CCH$_3$—O—.

Some preferred compounds of this group include:
(−)-(trans)-N-[[2-(2-benzofuran-4-yl)cycloprop-1-yl]methyl]cyclopropane carboxamide;
(−)-(trans)-N-[[2-(benzofuran-4-yl)cycloprop-1-yl]methyl]propanamide;
(trans)-N-[[2-(2-methyl-benzofuran-4-yl)cycloprop-1-yl]methyl]acetamide;
(trans)-N-[[2-(2-methyl-benzofuran-4-yl)cycloprop-1-yl]methyl]propanamide;
(trans)-N-[[2-(2-methyl-benzofuran-4-yl)cycloprop-1-yl]methyl]butanamide;
(trans)-N-[[2-(benzofuran-4-yl)cycloprop-1-yl]methyl]acetamide;
(trans)-N-[[2-(benzofuran-4-yl)cycloprop-1-yl]methyl]propanamide;
(trans)-N-[[2-(benzofuran-4-yl)cycloprop-1-yl]methyl]butanamide;
(trans)-N-[[2-(benzofuran-4-yl)cycloprop-1-yl]methyl]-2-methylpropanamide;
(trans)-N-[[2-(benzofuran-4-yl)cycloprop-1-yl]methyl]cyclopropane carboxamide; and
(trans)-N-[[2-(benzofuran-4-yl)cycloprop-1-yl]methyl]-N-methylurea.

A second group of preferred compounds include the dihydrobenzo-furans of Formula I wherein the group, —X—Y—Z—, consists of —CH$_2$—CH$_2$—O—, —CH$_2$—C(CH$_3$)$_2$—O— and —CH$_2$—CH(CH$_3$)—O—.

Some preferred compounds of this second group include:
(+)-N-[[2-(2,3-dihydrobenzofuran-4-yl)cycloprop-1-yl]methyl]propanamide;
(−)-(trans)-N-[[2-(2,3-dihydrobenzofuran-4-yl)cycloprop-1-yl]methyl]acetamide;
(−)-(trans)-N-[[2-(2,3-dihydrobenzofuran-4-yl)cycloprop-1-yl]methyl]butanamide;
(−)-(trans)-N-[[2-(2,3-dihydrobenzofuran-4-yl)cycloprop-1-yl]methyl]-N-methylurea;
(−)-(trans)-N-[[2-(2,3-dihydrobenzofuran-4-yl)cycloprop-1-yl]methyl]methoxyacetamide;
(−)-(trans)-N-[[2-(2,3-dihydrobenzofuran-4-yl)cycloprop-1-yl]methyl]cyclopropanecarboxamide;
(−)-(trans)-N-[[2-(2,3-dihydrobenzofuran-4-yl)cycloprop-1-yl]methyl]trifluoroacetamide;
(trans)-N-[[2-(2,3-dihydro-2,2-dimethyl-benzofuran-4-yl)cycloprop-1-yl]methyl]propanamide;
(trans)-N-[[2-(2,3-dihydro-2,2-dimethyl-benzofuran-4-yl)cycloprop-1-yl]methyl]butanamide;
(+)-(trans)-N-[[2-(2-methyl-2,3-dihydrobenzofuran-4-yl)cycloprop-1-yl]methyl]acetamide;
(+)-(trans)-N-[[2-(2-methyl-2,3-dihydrobenzofuran-4-yl)cycloprop-1-yl]methyl]propanamide;
(+)-(trans)-N-[[2-(2-methyl-2,3-dihydrobenzofuran-4-yl)cycloprop-1-yl]methyl]butanamide;
(+)-(trans)-N-[[2-(2-methyl-2,3-dihydrobenzofuran-4-yl)cycloprop-1-yl]methyl]cyclopropane carboxamide;
(+)-(trans)-N-[[2-(2-methyl-2,3-dihydrobenzofuran-4-yl)cycloprop-1-yl]methyl]-2-methylpropanamide;
(+)-(trans)-N-[[2-(2-methyl-2,3-dihydrobenzofuran-4-yl)cycloprop-1-yl]methyl]chloroacetamide;
(−)-(trans)-N-[[2-(2-methyl-2,3-dihydrobenzofuran-4-yl)cycloprop-1-yl]methyl]propanamide;
(−)-(trans)-N-[[2-(2-methyl-2,3-dihydrobenzofuran-4-yl)cycloprop-1-yl]-2-methylpropanamide;
(−)-(trans)-N-[[2-(2-methyl-2,3-dihydrobenzofuran-4-yl)cycloprop-1-yl]methyl]acetamide;
(−)-(trans)-N-[[2-(2-methyl-2,3-dihydrobenzofuran-4-yl)cycloprop-1-yl]methyl]methoxyacetamide;
(−)-(trans)-N-[[2-(2-methyl-2,3-dihydrobenzofuran-4-yl)cycloprop-1-yl]methyl]cyclopropane carboxamide;
(−)-(trans)-N-[[2-(2-methyl-2,3-dihydrobenzofuran-4-yl)cycloprop-1-yl]methyl]butanamide;
(trans)-N-[[2-(2,3-dihydrobenzofuran-4-yl)cycloprop-1-yl]methyl]acetamide;
(−)-(trans)-N-[[2-(2,3-dihydrobenzofuran-4-yl)cycloprop-1-yl]methyl] propanamide;
(trans)-N-[[2-(2,3-dihydrobenzofuran-4-yl)cycloprop-1-yl]methyl] propanamide;
(trans)-N-[[2-(2,3-dihydrobenzofuran-4-yl)cycloprop-1-yl]methyl] butanamide;
(trans)-N-[[2-(2,3-dihydro-5,7-diiodobenzofuran-4-yl)cyclopropyl]methyl]propanamide; and
(trans)-N-[[2-(2,3-dihydro-5-iodobenzofuran-4-yl)cyclopropyl]methyl]-propanamide.

A third group of preferred compounds include the benzodioxoles of Formula I wherein the group, —X—Y—Z—, consists of —O—CH$_2$—O—.

Some preferred compounds in the third group include:
(trans)-N-[[2-(1,3-benzodioxol-4-yl)cycloprop-1-yl]methyl]acetamide;
(−)-(trans)-N-[[2-(1,3-benzodioxol-4-yl)cycloprop-1-yl]methyl]acetamide;
(trans)-N-[[2-(1,3-benzodioxol-4-yl)cycloprop-1-yl]methyl]propanamide;
(−)-(trans)-N-[[2-(1,3-benzodioxol-4-yl)cycloprop-1-yl]methyl] propanamide;
(trans)-N-[[2-(1,3-benzodioxol-4-yl)cycloprop-1-yl]methyl]butanamide;
(−)-(trans)-N-[[2-(1,3-benzodioxol-4-yl)cycloprop-1-yl]methyl] butanamide;
(trans)-N-[[2-(1,3-benzodioxol-4-yl)cycloprop-1-yl]methyl]cyclopropane carboxamide;
(−)-(trans)-N-[[2-(1,3-benzodioxol-4-yl)cycloprop-1-yl]methyl] cyclopropane carboxamide;

(trans)-N-[[2-(1,3-benzodioxol-4-yl)cycloprop-1-yl]methyl]-2-methylpropanamide;
(-)-(trans)-N-[2-(1,3-benzodioxol-4-yl) cycloprop-1-yl]methyl]-2-methylpropanamide;
(trans)-N-[[2-(1,3-benzodioxol-4-yl)cycloprop-1-yl]methyl]-N'-ethylurea; and
(-)-(trans)-N-[[2-(1,3-benzodioxol-4-yl)cycloprop-1-yl]methyl]-N'-ethylurea.

Another group of preferred compounds include the benzodioxanes of Formula I wherein the group, —X—Y—Z—, consists of —O—(CH$_2$)$_2$—)—.

Some preferred benzodioxanes include:
(-)-(trans)-N-[[2-(2,3-dihydro-1,4-benzodioxin-5-yl)cycloprop-1-yl]methyl]propanamide;
(-)-(trans)-N-[[2-(2,3-dihydro-1,4-benzodioxin-5-yl)cycloprop-1-yl]methyl]acetamide;
(+)-(trans)-N-[[2-(2,3-dihydro-1,4-benzodioxin-5-yl)cycloprop-1-yl]methyl]-N-methylurea
(+)-(trans)-N-[[2-(2,3-dihydro-1,4-benzodioxin-5-yl)cycloprop-1-yl]methyl]-2-methoxyacetamide;
(-)-(trans)-N-[[2-(2,3-dihydro-1,4-benzodioxin-5-yl)cycloprop-1-yl]methyl]cyclopropanecarboxamide;
(-)-(trans)-N-[[2-(2,3-dihydro-1,4-benzodioxin-5-yl)cycloprop-1-yl]methyl]butanamide;
(+)-(trans)-N-[[2-(2,3-dihydro-1,4-benzodioxin-5-yl)cycloprop-1-yl]methyl]propanamide;
(-)-(trans)-N-[[2-(2,3-dihydro-1,4-benzodioxin-5-yl)cycloprop-1-yl]methyl]trifluoroacetamide;
(-)-(trans)-N-[[2-(2,3-dihydro-1,4-benzodioxin-5-yl)cycloprop-1-yl]methyl]-3,3,3-trifluoropropanamide;
(+)-(trans)-N-[[2-(2,3-dihydro-1,4-benzodioxin-5-yl)cycloprop-1-yl]methyl]propanamide;
(trans)-N-[[2-(2,3-dihydro-1,4-benzodioxin-5-yl)cycloprop-1-yl]-methyl]acetamide;
(trans)-N-[[2-(2,3-dihydro-1,4-benzodioxin-5-yl)cycloprop-1-yl]-methyl]propanamide;
(trans)-N-[(2-(2,3-dihydro-1,4-benzodioxin-5-yl)cycloprop-1-yl]-methyl]butanamide;
(trans)-N-[[2-(2,3-dihydro-1,4-benzodioxin-5-yl)cycloprop-1-yl]methyl]-2-methylpropanamide;
(trans)-N-[[2-(2,3-dihydro-1,4-benzodioxin-5-yl)cycloprop-1-yl]-methyl]cyclopropane carboxamide;
(trans)-N-[[2-(2,3-dihydro-1,4-benzodioxin-5-yl)cycloprop-1-yl]methyl]-N-methylurea; and
(trans)-N-[[2-(2,3-dihydro-1,4-benzodioxin-5-yl)cycloprop-1-yl]methyl]-N-ethylurea.

Still another group of preferred compounds include the benzofurans of Formula I wherein the group, —X—Y—Z, consists of —O—CH=CH— and —O—CCH$_3$=CH—.

Some preferred compounds of this group include:
(trans)-N-[[2-(benzofuran-7-yl)cycloprop-1-yl]methyl]acetamide;
(trans)-N-[[2-(benzofuran-7-yl)cycloprop-1-yl]methyl]propanamide;
(trans)-N-[[2-(benzofuran-7-yl)cycloprop-1-yl]methyl]butanamide; and
(trans)-N-[[2-(benzofuran-7-yl)cycloprop-1-yl]methyl]-cyclopropanecarboxamide.

Still yet another group of preferred compounds include the benzopyrans of Formula I wherein the group, —X—Y—Z, consists of —CH$_2$—(CH$_2$)$_2$—O—.

Some preferred compounds of this group include:
(trans)-N-[[2-(3,4-dihydro-2H-1-benzopyran-5-yl)cycloprop-1-yl]methyl]propanamide;
(trans)-N-[[2-(3,4-dihydro-2H-1-benzopyran-5-yl)cycloprop-1-yl]methyl]cyclopropane carboxamide;
(-)-(trans)-N-[[2-(3,4-dihydro-2H-1-benzopyran-5-yl)cycloprop-1-yl]methyl]propanamide;
(-)-(trans)-N-[[2-(3,4-dihydro-2H-1-benzopyran-5-yl)cycloprop-1-yl]methyl]acetamide;
(trans)-N-[[2-(3,4-dihydro-2H-1-benzopyran-5-yl)cycloprop-1-yl]methyl]butanamide; and
(+)-(trans)-N-[[2-(3,4-dihydro-2H-1-benzopyran-5-yl)cycloprop-1-yl]methyl]propanamide.

Additionally, compounds of Formula I encompass all pharmaceutically acceptable solvates, particularly hydrates, thereof. The present invention also encompasses diastereomers as well as optical isomers, e.g. mixtures of enantiomers including racemic mixtures, as well as individual enantiomers and diastereomers, which arise as a consequence of structural asymmetry in certain compounds of Formula I. Separation of the individual isomers or selective synthesis of the individual isomers is accomplished by application of various methods which are well known to practitioners in the art.

Compounds of Formula I can be prepared using the overall processes shown in the following Reaction Schemes:

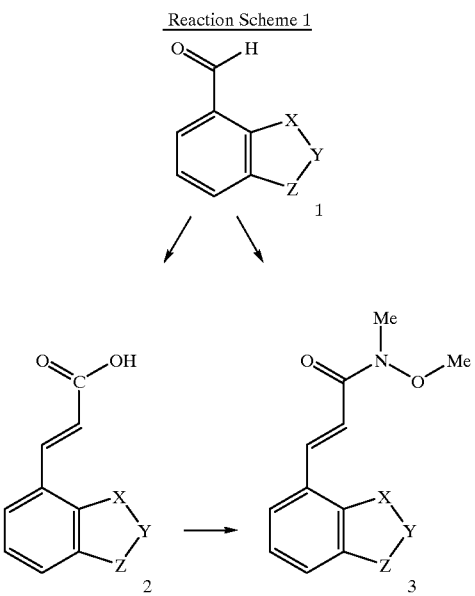

The syntheses of the 4-aryl-propenoic acid derivatives, 2 and 3, are shown in Reaction Scheme 1. The starting aldehydes, 1, can be prepared by methods well known to those skilled in the art. Condensation of malonic acid with the aldehydes, 1, in solvents such as pyridine with catalysts such as piperidine or pyrrolidine, gives the 4-aryl-propenoic acid, 2. Subsequent conversion of the acid to the acid chloride using reagents such as thionyl chloride, phosphoryl chloride, or the like, followed by reaction with N,O-dimethyl hydroxylamine gives the amide intermediate 3 in good yields. Alternatively, aldehyde 1 can be converted directly to amide 3 using reagents such as diethyl (N-methoxy-N-methyl-carbamoylmethyl)phosphonate with a strong base such as sodium hydride.

Reaction Scheme 2

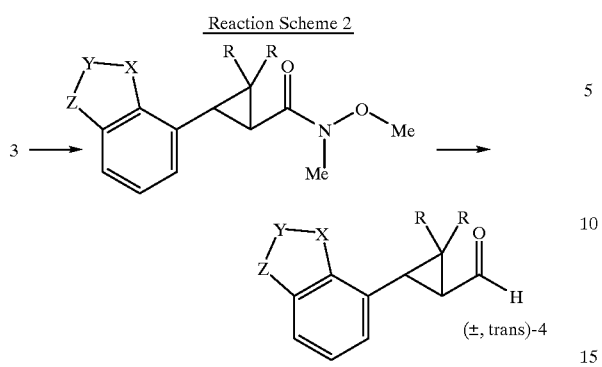

(±, trans)-4

The conversion of the amide intermediate 3 to the racemic, transcyclopropane carboxaldehyde intermediate, 4, is shown in Reaction Scheme 2. Intermediate 3 was allowed to react with cyclopropanating reagents such as trimethyl-sulfoxonium iodide and sodium hydride in solvents such as DMF, THF, or the like. Subsequent reduction using reagents such as LAH in solvents such as THF, ethyl ether, or the like, gives the racemic, trans-cyclopropane carboxaldehyde intermediates, 4.

Reaction Scheme 3

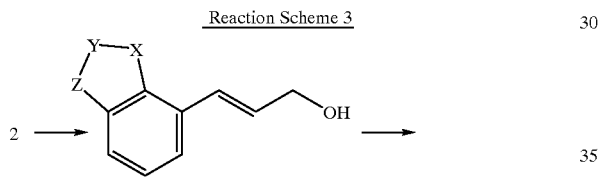

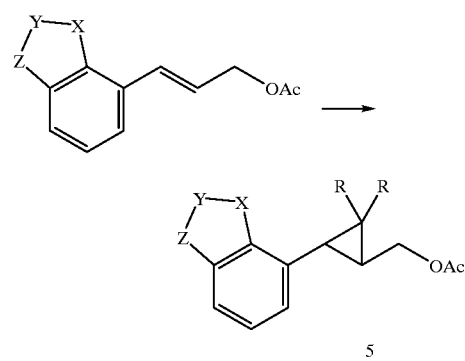

Racemic cyclopropane intermediate 5 (R=halogen) can be prepared from intermediate 2 as shown in Reaction Scheme 3. Intermediate 2 was converted to the corresponding allylic alcohol by treatment with reducing agents such as sodium borohydride plus iodine in solvents such as THF. Subsequent acylation using reagents such as acetic anhydride in pyridine or acetyl chloride gave the allylic acetate which was allowed to react with cyclopropanating reagents such as sodium chloro-difluoroacetate in diglyme to provide the racemic, transcyclopropane acetate intermediates, 5.

Reaction Scheme 4

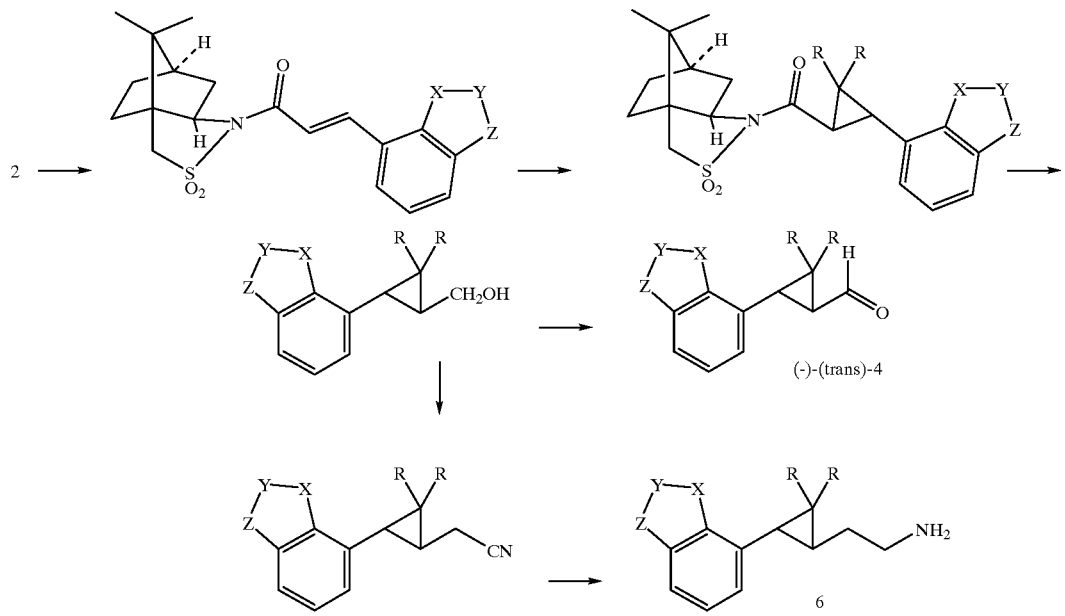

(-)-(trans)-4

The conversion of the acid 2 to the chiral cyclopropane carboxaldehyde intermediate, (−)-(trans)-4, is shown in Reaction Scheme 4. Intermediate 2 is condensed with (−)-2,10-camphorsultam under standard conditions, and then cyclopropanated in the presence of catalysts such as palladium acetate using diazomethane generated from reagents such as 1-methyl-3-nitro-1-nitrosoguanidine. Subsequent reduction using reagents such as LAH in solvents such as THF, followed by oxidation of the alcohol intermediates using reagents such as DMSO/oxalyl chloride, or PCC, gives the cyclopropane carboxaldehyde intermediate, (−)-(trans)-4, in good yields. The enantiomer, (+)-(trans)-4, can also be obtained employing a similar procedure using (+)-2,10-camphorsultam in place of (−)-2,10-camphorsultam.

When it is desired to prepare compounds of Formula I wherein m=2, the alcohol intermediate may be activated in the conventional manner such as with mesyl chloride and treated with sodium cyanide followed by reduction of the nitrile group with a reducing agent such as LAH to produce the amine intermediate 6.

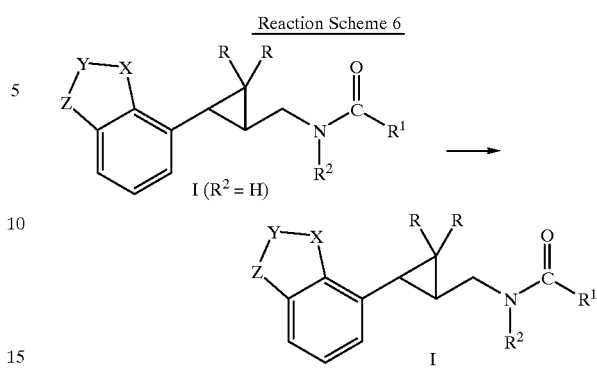

Reaction Scheme 6 shows the alkylation of secondary amides of Formula I ($R^2$=H) to give tertiary amides of Formula I ($R^2$=alkyl). The secondary amide is reacted with a base such as sodium hydride, potassium tert-butoxide, or the like, and then reacted with an alkylating reagent such as alkyl halides, alkyl sulfonate esters, or the like to produce tertiary amides of Formula I.

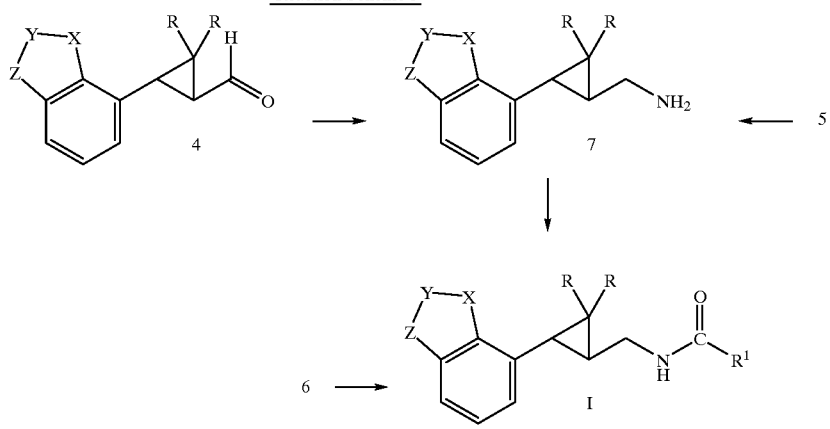

Reaction Scheme 5 shows the conversion of intermediates 4 and 5 to the amine intermediate, 7, and the subsequent conversion of 6 or 7 to compounds of Formula I. The carboxaldehyde intermediate, 4, is condensed with hydroxylamine and then reduced with reagents such as LAH to give the amine intermediate, 7. The acetate intermediate 5 is hydrolyzed with potassium hydroxide to the alcohol, converted to the mesylate with methane sulfonyl chloride and triethyl amine in $CH_2Cl_2$ and then converted to the azide by treatment with sodium azide in solvents such as DMF. Subsequent reduction of the azide group with a reducing agent such as LAH produced the amine intermediate 7. Further reaction of 6 or 7 with acylating reagents gives compounds of Formula I. Suitable acylating agents include carboxylic acid halides, anhydrides, acyl imidazoles, alkyl isocyanates, alkyl isothiocyanates, and carboxylic acids in the presence of condensing agents, such as carbonyl imidazole, carbodiimides, and the like.

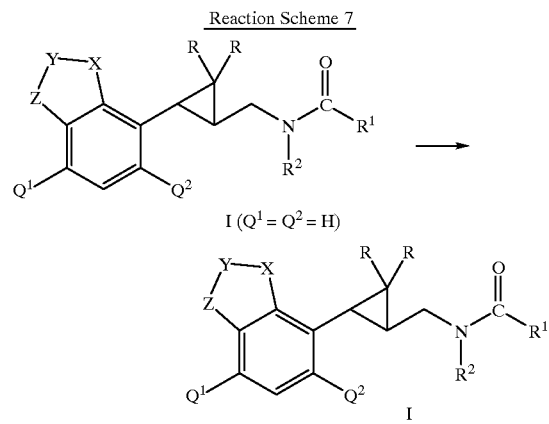

Reaction Scheme 7 shows the halogenation of compounds of Formula I. The carboxamides, I ($Q^1$=$Q^2$=H), are reacted with excess amounts of halogenating agents such as iodine, N-bromosuccinimide, or the like to give the dihalocompounds of Formula I ($Q^1=Q^2$=halogen). Alternatively, a stoichiometric amount of these halogenating agents can be used to give the monohalo-compounds of Formula I ($Q^1$=H, $Q^2$=halogen; or $Q^1$=halogen, $Q^2$=H). In both cases, additives such as lead IV tetraacetate can be used to facilitate the reaction.

Biological Activity of the Compounds

The compounds of the invention are melatonergic agents. They have been found to bind human melatonergic receptors expressed in a stable cell line with good affinity. Further, the compounds are agonists as determined by their ability, like melatonin, to block the forskolin-stimulated accumulation of cAMP in certain cells. Due to these properties, the compounds and compositions of the invention should be useful as sedatives, chronobiotic agents, anxiolytics, antipsychotics, analgesics, and the like. Specifically, these agents should find use in the treatment of stress, sleep disorders, seasonal depression, appetite regulation, shifts in circadian cycles, melancholia, benign prostatic hyperplasia and related conditions.

Melatonergic Receptor Binding Activity

1. Reagents:

(a) TME=50 mM Tris buffer containing 12.5 mM $MgCl_2$, and 2 mM EDTA, pH 7.4 at 37° C. with concentrated HCl.

(b) Wash buffer: 20 mM Tris base containing 2 mM $MgCl_2$, pH 7.4 at room temperature.

(c) $10^{-4}$M melatonin ($10^{-5}$M final concentration).

(d) 2-[$^{125}$I]-iodomelatonin, 0.1M final concentration

2. Membrane Homogenates:

The melatonin $ML_{1a}$ receptor cDNA was subcloned into pcDNA3 and introduced into NIH-3T3 cells using Lipofectamine. Transformed NIH-3T3 cells resistant to geneticin (G-418) were isolated, and single colonies expressing high levels of 2[$^{125}$I]-iodomelatonin binding were isolated. Cells are maintained in DMEM supplemented with 10% calf serum and G-418 (0.5 g/liter). Cells are grown to confluency in T-175 flasks, scraped using Hank's balanced salt solution, and frozen at −80° C. For preparing membrane homogenates, pellets are thawed on ice, and resuspended in TME buffer in the presence of 10 µg/ml aprotinin and leupeptin, and 100 µM phenylmethylsulfonylfluoride. The cells were then homogenized using a dounce homogenizer, and centrifuged. The resulting pellet was resuspended with dounce homogenizer in TME (supplemented with the above protease inhibitors) and frozen. On the day of assay, the small aliquot was thawed on ice and resuspended in ice cold TME (1:50–1:100 v/v) and held on ice until assayed.

3. Incubation: 37° C. for 1 hour. Reaction is terminated by filtration. Filters are washed 3 times.

4. References: Reppert, et al., *Neuron*, 13, p. 1177–1185 (1994).

The binding data for some compounds of Formula I are shown in Table 1.

TABLE 1

Melatonin Binding for some Compounds of Formula I

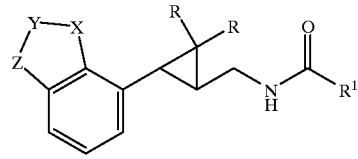

| Ex. No. | R | $R^1$ | X—Y—Z | Melatonin Binding Affinity ($IC_{50}$)[a] |
|---|---|---|---|---|
| 2 | H | Et | $CH_2$—$CH_2$—O | +++ |
| 3 | H | Me | O—$CH_2$—O | +++ |
| 11 | H | iPr | O—$CH_2$—O | ++ |
| 18 | H | cPr | O—$(CH_2)_2$—O | ++ |
| 23 | H | Et | CH=CH—O | +++ |
| 29 | H | Et | $CH_2$—$CH_2$—O | +++ |
| 30 | H | nPr | $CH_2$—$CH_2$—O | +++ |
| 42 | H | Et | $CH_2$—$(CH_2)_2$—O | ++ |
| 51 | H | NHEt | O—$(CH_2)_2$—O | + |
| 52 | H | vinyl | O—$(CH_2)_2$—O | +++ |
| 54 | H | $CF_3$ | O—$(CH_2)_2$—O | +++ |
| 60 | H | Me | O—$(CH_2)_3$—O | ++ |
| 61 | H | Et | $CH_2$—$(CH_2)_3$—O | + |
| 67 | H | cPr | O—$CH_2$—$CH_2$ | ++ |
| 76 | H | nPr | CH=CMe—O | +++ |
| 80 | H | cPr | O—CH=CH | ++ |
| 82 | H | Et | $CH_2$—(CHMe)—O | +++ |
| 88 | H | Et | $CH_2$—(CHMe)—O | +++ |
| 95 | F | Et | CH=(CMe)—O | ++ |
| 96 | H | Et | $CH_2$—$(CH_2)_2$—O | +++ |

[a]= $IC_{50}$ values for $ML_{1a}$ human melatonin receptor binding
+ = 250 nM > $IC_{50}$ > 100 nM
++ = 100 nM > $IC_{50}$ > 10 nM
+++ = 10 nM > $IC_{50}$ The compounds of the present invention have affinity for receptors of the endogenous pineal hormone, melatonin, as determined in a receptor binding assays, as described above in Table 1 for the $ML_{1a}$ (human) receptors. Melatonin is involved in the regulation of a variety of biological rhythms and exerts its biological effects via interaction with specific receptors. There is evidence that administration of melatonin agonists are of clinical utility in the treatment of various conditions regulated by melatonin activity. Such conditions include depression, jet-lag, work-shift syndrome, sleep disorders, glaucoma, some disorders associated with reproduction, cancer, benign prostatic hyperplasia, immune disorders and neuroendocrine disorders.

For therapeutic use, the pharmacologically active compounds of Formula I will normally be administered as a pharmaceutical composition comprising as the (or an) essential active ingredient at least one such compound in association with a solid or liquid pharmaceutically acceptable carrier and, optionally, with pharmaceutically acceptable adjuvants and excipients employing standard and conventional techniques.

The pharmaceutical compositions include suitable dosage forms for oral, parenteral (including subcutaneous, intramuscular, intradermal and intravenous) transdermal, bronchial or nasal administration. Thus, if a solid carrier is used, the preparation may be tableted, placed in a hard gelatin capsule in powder or pellet form, or in the form of a troche or lozenge. The solid carrier may contain conventional excipients such as binding agents, fillers, tableting lubricants, disintegrants, wetting agents and the like. The tablet may, if desired, be film coated by conventional techniques. If a liquid carrier is employed, the preparation may be in the form of a syrup, emulsion, soft gelatin capsule, sterile vehicle for injection, an aqueous or non-aqueous liquid suspension, or may be a dry product for reconstitution with water or other suitable vehicle before use. Liquid preparations may contain conventional additives such as suspending agents, emulsifying agents, wetting agents, non-aqueous vehicle (including edible oils), preservatives, as well as flavoring and/or coloring agents. For parenteral administration, a vehicle normally will comprise sterile water, at least in large part, although saline solutions, glucose solutions and like may be utilized. Injectable suspensions also may be used, in which case conventional suspending agents may be employed. Conventional preservatives, buffering agents and the like also may be added to the parenteral dosage forms. Particularly useful is the administration of a compound of Formula I in oral dosage formulations. The pharmaceutical compositions are prepared by conventional techniques appropriate to the desired preparation containing appropriate amounts of the active ingredient, that is, the compound of Formula I according to the invention. See, for example, *Remington's Pharmaceutical Sciences,* Mack Publishing Company, Easton, Pa., 17th edition, 1985.

In making pharmaceutical compositions containing compounds of the present invention, the active ingredient(s) will usually be mixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the composition can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions and sterile packaged powders.

Some examples of suitable carriers and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, methyl cellulose, methyl- and propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide quick, sustained or delayed release of the active ingredient after administration to the patient.

The dosage of the compounds of Formula I to achieve a therapeutic effect will depend not only on such factors as the age, weight and sex of the patient and mode of administration, but also on the degree of melatonergic activity desired and the potency of the particular compound being utilized for the particular disorder or condition concerned. It is also contemplated that the treatment and dosage of the particular compound may be administered in unit dosage form and that the unit dosage form would be adjusted accordingly by one skilled in the art to reflect the relative level of activity. The decision as to the particular dosage to be employed (and the number of times to be administered per day) is within the discretion of the physician, and may be varied by titration of the dosage to the particular circumstances of this invention to produce the desired therapeutic effect.

The compositions are preferably formulated in a unit dosage form, each dosage containing from about 0.1 to 100 mg, more usually 1 to 10 mg, of the active ingredient. The term "unit dosage form" refers to physically discrete units suitable as unitary dosages for human subjects and other mammals, each unit containing a predetermined quantity of active material calculated to produce the desired therapeutic effect, in association with the required pharmaceutical carrier.

These active compounds are effective over a wide dosage range. For example, dosages per day will normally fall within the range of about 0.1 to 500 mg. In the treatment of adult humans, the range of about 0.1 to 10 mg/day, in single or divided doses, is preferred. Generally, the compounds of the invention may be used in treating sleep and related disorders in a manner similar to that used for melatonin.

However, it will be understood that the amount of the compound actually administered will be determined by a physician, in the light of the relevant circumstances including the condition to be treated, the choice of compound to be administered, the chosen route of administration, the age, weight, and response of the individual patient, and the severity of the patient's symptoms.

The compounds which constitute this invention, their methods of preparation and their biologic actions will appear more fully from consideration of the following examples, which are given for the purpose of illustration only and are not to be construed as limiting the invention in sphere or scope.

DESCRIPTION OF SPECIFIC EMBODIMENTS

In the following examples, used to illustrate the foregoing synthetic processes, all temperatures are expressed in degrees Celsius and melting points are uncorrected. Proton magnetic resonance ($^1$H NMR) spectra were determined in the solvents indicated and chemical shifts are reported in δ units downfield from the internal standard tetramethylsilane (TMS) and interproton coupling constants are reported in Hertz (Hz). Splitting patterns are designated as follows: s, singlet; d, doublet; t, triplet; q, quartet; m, multiplet; br, broad peak; dd, doublet of doublet; bd, broad doublet; dt, doublet of triplet; bs, broad singlet; dq, doublet of quartet. The infrared (IR) spectral descriptions include only absorption wave numbers (cm$^{-1}$) having functional group identification value. The IR determinations were employed using the compound neat as a film or by employing potassium bromide (KBr) as diluent. Optical rotations $[\alpha]_D^{25}$ were determined in the solvents and concentration indicated. The elemental analyses are reported as percent by weight.

Preparation of Intermediates of Formula 1

Preparation 1

Benzofuran-4-carboxaldehyde

Step 1: N-Methoxy-N-methyl-benzofuran-4-carboxamide

A mixture of benzofuran-4-carboxylic acid [Eissenstat, et al., J. Medicinal Chemistry, 38 (16) 3094–3105 (1995)] (2.8 g, 17.4 mmol) and thionyl chloride (25 mL) was heated to reflux for 2 h and then concentrated in vacuo. The solid residue was dissolved in ethyl acetate (50 mL) and a solution of N,O-dimethylhydroxylamine hydrochloride (2.8 g) in saturated NaHCO$_3$ (60 mL) was added with stirring. After stirring for 1.5 h, the ethyl acetate layer was separated. The aqueous layer was extracted with ethyl acetate. The ethyl acetate extracts were combined, washed with saturated NaHCO$_3$ and concentrated in vacuo to give an oil (3.2 g, 95.4%).

Step 2: Benzofuran-4-carboxaldehyde

A solution of N-methoxy-N-methyl-benzofuran-4-carboxamide (3.2 g, 16.6 mmol) in THF (100 mL) was cooled to −45° C. and then LAH (0.7 g, 18.7 mmol) was added. The mixture was stirred for 15 min, allowed to warm to −5° C., and then recooled to −45° C. Saturated KHSO$_4$ (25 mL) was added with vigorous stirring, and the mixture was allowed to warm to room temperature. The precipitate was filtered and washed with acetone. The filtrate was concentrated in vacuo to give an oil (2.3 g, 94%).

Preparation 2
2,3-Dihydrobenzofuran-4-carboxaldehyde

Step 1: 2,3-Dihydrobenzofuran-4-carboxylic acid

Benzofuran-4-carboxylic acid (10.0 g, 61.7 mmol) was hydrogenated (60 psi) in acetic acid (100 mL) over 10% Pd/C (2 g) for 12 hr. The mixture was filtered and the filtrate was diluted with water (500 mL) to give 2,3-dihydrobenzofuran-4-carboxylic acid as a white powder (8.4 g, 83%). A sample was recrystallized from isopropanol to give fine white needles (mp: 185.5–187.5° C).

Step 2: (2,3-Dihydrobenzofuran-4-yl)methanol

A solution of 2,3-dihydrobenzofuran-4-carboxylic acid (10 g, 61 mmol) in THF (100 mL) was stirred as LAH (4.64 g, 122 mmol) was slowly added. The mixture was heated to reflux for 30 min. The mixture was cooled and quenched cautiously with ethyl acetate and then with 1N HCl (150 mL). The mixture was then made acidic with 12N HCl until all the inorganic precipitate dissolved. The organic layer was separated, and the inorganic layer was extracted twice with ethyl acetate. The organic layers were combined, washed twice with brine, and then concentrated in vacuo. This oil was Kugelrohr distilled to a clear oil that crystallized upon cooling (8.53 g, 87.6%).

Step 3: 2,3-Dihydrobenzofuran-4-carboxaldehyde

DMSO (8.10 mL, 114 mmol) was added at −78° C. to a stirred solution of oxalyl chloride in CH$_2$Cl$_2$ (40 mL of a 2M solution). A solution of (2,3-dihydrobenzofuran-4-yl) methanol (8.53 g, 56.9 mmol) in CH$_2$Cl$_2$ (35 mL) was added dropwise, and the solution stirred at −78° C. for 30 min. Triethyl amine (33 mL, 228 mmol) was added cautiously to quench the reaction. The resulting suspension was stirred at room temperature for 30 min and diluted with CH$_2$Cl$_2$ (100 mL). The organic layer was washed three times with water, and twice with brine, and then concentrated in vacuo to an oil (8.42 g, 100%) that was used without purification.

Preparation 3
2,3,4,5-Tetrahydrobenzoxepin-6-carboxaldehyde

Step 1: Ethyl 2-allyl-3-benzyloxybenzoate

A mixture of ethyl 2-allyl-3-hydroxybenzoate (20.6 g, 100 mmol), benzyl bromide (18 g, 105 mmol), and potassium carbonate (17 g, 123 mmol), was heated in DMF to 100° C. for 18 hr. The mixture was cooled and diluted with water (500 ml), and extracted with ethyl acetate three times. The ethyl acetate extracts were dried over brine and concentrated in vacuo to a tan oil (29.6 g, 100%).

Step 2: Ethyl 2-(3-hydroxypropyl)-3-benzyloxybenzoate

A solution of ethyl 2-allyl-3-benzyloxybenzoate (29.6 g, 100 mmol) in THF (300 ml) was cooled to −10° C. under nitrogen. A solution of borane THF complex (110 ml of 1M, 110 mmol) was added dropwise, and the reaction mixture was allowed to warm to room temperature and stirred for 1 hr. A solution of hydrogen peroxide (12 ml) in saturated NaHCO3 (200 ml) was then slowly added, and the mixture was stirred for 30 min. The mixture was extracted with ethyl acetate twice. The ethyl acetate extracts were washed with water, dried over brine, and then concentrated in vacuo to give a clear oil (27.6 g, 88%).

Step 3: Ethyl 2-(3-methanesulfonyloxypropyl)-3-benzyloxybenzoate

A solution of ethyl 2-(3-hydroxypropyl)-3-benzyloxybenzoate (10.19 g, 32.5 mmol), and triethyl amine (4.05 g, 40 mmol) in methylene chloride (100 ml) was cooled in an ice bath as methane sulfonyl chloride (2.79 ml, 36 mmol) was slowly added. The ice bath was removed and the reaction allowed to warm to room temperature over a 1 hr period. The mixture was diluted with water, and the methylene chloride layer was separated. The methylene chloride layer was washed with water twice, 1N HCl twice, and then filtered through a pad of silica gel to give a clear solution. This solution was concentrated in vacuo to give a clear oil (12.4 g, 98%).

Step 4: Ethyl 2-(3-cyanopropyl)-3-benzyloxybenzoate

A mixture of ethyl 2-(3-methanesulfonyloxypropyl)-3-benzyloxybenzoate (19.42 g, 31.7 mmol) and potassium cyanide (2.28 g, 35 mmol) in DMF (50 ml) was heated at 100° C. for 8 hr. The mixture was cooled, diluted with water (250 ml), and extracted three times with ethyl acetate. The ethyl acetate extracts were dried with brine, and concentrated in vacuo. The crude product was chromatographed on silica gel using methylene chloride as the eluent to give the product as an oil (5.25 g, 53%).

Step 5: 4-[2-Benzyloxy-6-carboxyphenyl]butanoic acid

A mixture of ethyl 2-(3-cyanopropyl)-3-benzyloxybenzoate (5.25 g, 16.9 mmol) in 5N sodium hydroxide (75 ml) was heated to reflux for 18 hr. The solution was cooled and made acidic with 12N HCl. The white precipitate was collected and air dried (5 g, 94%).

Step 6: 4-[2-Hydroxy-6-carboxy-phenyl]butanoic acid

A solution of 4-[2-benzyloxy-6-carboxy-phenyl]butanoic acid (5 g, 15.9 mmol) in ethanol was hydrogenated at 60 psi for 4 hr over 10% Pd/C (1 g). The mixture was filtered, and the filtrate was concentrated in vacuo to give a white solid (3.95 g, 99%)

Step 7: Ethyl 4-[2-ethoxycarbonyl-6-hydroxyphenyl] butanoic acid

A solution of 4-[2-hydroxy-6-carboxyphenyl]butanoic acid (7.84 g, 35 mmol) in ethanol and sulfuric acid (10 drops) was heated to reflux for 18 hr. The solution was neutralized with sodium bicarbonate and cooled. The mixture was filtered and the filtrate was concentrated in vacuo. The resulting oil was dissolved in ethyl acetate, washed with water, dried with brine, and the concentrated in vacuo to give the product as an oil (9.06 g, 92.4%).

Step 8: 4-[2-Ethoxycarbonyl-6-hydroxyphenyl]butanoic acid

Ethyl 4-[2-ethoxycarbonyl-6-hydroxyphenyl]butanoic acid (9.06 9, 32.4 mmol) was dissolved in a room temperature solution of potassium hydroxide (3.62 g, 64.6 mmol) in water (68 ml). The solution was stirred at room temperature for 2 hr, and then made acidic with 12N HCl. The mixture was extracted twice with ethyl acetate. The ethyl acetate extracts were combined and extracted with 10% aqueous potassium carbonate three times. These aqueous extracts were made acidic with 12N HCl and extracted twice with ethyl acetate. The ethyl acetate extracts were concentrated in vacuo to a white solid (6.4 g, 79%).

Step 9: 4-[2-Ethoxycarbonyl-6-hydroxyphenyl]butan-1-ol

Borane THF complex (56 ml of 1M in THF, 56 mmol) was slowly added to a solution of 4-[2-ethoxycarbonyl-6-hydroxyphenyl]butanoic acid in THF at 0° C. The solution was stirred for 2 hr and allowed to warm to room temperature. The reaction was quenched slowly with aqueous acetic acid (5 ml of 50%) and stirred until the bubbling subsided. The mixture was concentrated in vacuo to a slurry, which was dissolved in cold 10% potassium carbonate. The solution was extracted with ethyl acetate twice. The organic extracts were dried with brine and concentrated in vacuo to a tan oil that solidified upon standing (5.14 g, 84.9%).

Step 10: Ethyl 2,3,4,5-tetrahydrobenzoxepin-6-carboxylate

A solution of 4-[2-ethoxycarbonyl-6-hydroxyphenyl]butan-1-ol (5.14 g, 21.6 mmol) in THF (20 ml) was added dropwise to an ice bath cooled solution of triphenyl phosphine (7.37 g, 28.1 mmol) and diethyl azodicarboxylate (4.89 g, 28.1 mmol) in THF (60 ml). The reaction was stirred for 18 hr and then concentrated in vacuo. The residue was purified by chromatography on silica gel using methylene chloride as the eluent to give the product as an oil (2.85 g, 60%).

Step 11: 2,3,4,5-Tetrahydrobenzoxepin-6-methanol

A solution of ethyl 2,3,4,5-tetrahydrobenzoxepin-4-carboxylate (2.85 g, 13 mmol) in THF (30 ml) was stirred as LAH (1 g, 26 mmol) was slowly added. The mixture was stirred for 18 hr, and then quenched by the sequential addition of water (1 ml), 15% sodium hydroxide (1 ml), and water (3 ml). The mixture was filtered and the filter cake washed with ethanol. The filtrate was concentrated in vacuo to an oil (2.3 g, 100%).

Step 12: 2,3,4,5-Tetrahydrobenzoxepin-6-carboxaldehyde

DMSO (1.85 ml, 26 mmol) was added slowly to a −78° C. solution of oxalyl chloride in methylene chloride (10 ml of 2M, 20 mmol). To this solution was added slowly a solution of 2,3,4,5-tetrahydrobenzoxepin-4-methanol (2.3 g, 13 mmol) in methylene chloride, and the mixture was stirred 30 min at −78° C. Triethyl amine (7.53 ml, 52 mmol) was added slowly to the reaction mixture, which was then allowed to warm to room temperature. The mixture was diluted with methylene chloride (50 ml) and washed with water and then brine. The organic layer was concentrated in vacuo to an oil (2.28 g, 100%).

Preparation 4
Benzofuran-7-carboxaldehyde

Step 1: Methyl 2-allyloxybenzoate

A mixture of allyl bromide (152.4 g, 1.27 mol), methyl salicylate (162.44 g, 1.06 mol), and potassium carbonate (219.75 g, 1.59 mol) in THF (600 ml) and DMF (600 ml) was heated to reflux for 6 hr. The mixture was poured into water (3L) and extracted with ethyl acetate three times. The ethyl acetate extracts were combined and washed with water and dried with brine. The ethyl acetate extracts were concentrated in vacuo to a yellow oil that was vacuum distilled to a clear oil (163.45 g, 80%).

Step 2: Methyl 3-allyl-salicylate

Methyl 2-allyloxybenzoate (163.5 g, 848 mmol) was heated to 220° C. for 1 hr, and then vacuum distilled to give the product (163.5 g, 100%).

Step 3: Methyl benzofuran-7-carboxylate

Ozone was bubbled through a solution of methyl 3-allyl-salicylate (30 g, 156 mmol) at −78° C. for 2 hr until no starting material was present on TLC. The reaction was quenched with dimethyl sulfide and stirred at room temperature for 18 hr. The mixture was concentrated in vacuo, and the residue was dissolved in ether. The ether solution was washed with brine three times, and then concentrated in vacuo to a green oil. This oil was dissolved in toluene and heated to reflux with sulfuric acid (0.5 ml) for 4 hr. Sodium carbonate (5 g) was added, and the mixture was cooled and then filtered. The filtrated was concentrated in vacuo to a dark oil that was purified by chromatography on silica gel using methylene chloride as the eluent to give the product as a green oil (12 g, 44%).

Step 4: Benzofuran-7-methanol

A solution of methyl benzofuran-7-carboxylate (5.34 g, 30 mmol) was added to a suspension of LAH (2.31 g, 61 mmol) in THF and then heated to reflux for 30 min. The reaction was quenched with ethyl acetate and water. The mixture was made acidic with 12N HCl until all the precipitate dissolved. The ethyl acetate layer was separated, washed with water, dried with brine, and concentrated in vacuo to give a yellow oil (4.03 g, 91%).

Step 5: Benzofuran-7-carboxaldehyde

DMSO (2.87 ml, 40 mmol) was added slowly to a −78° C. solution of oxalyl chloride in methylene chloride (20 ml of 2M, 40 mmol). To this solution was added slowly a solution of benzofuran-7-methanol (4.03 g, 27 mmol) in methylene chloride, and the mixture was stirred 30 min at −78° C. Triethyl amine (30 ml) was added slowly to the reaction mixture, which was then allowed to warm to room temperature. The mixture was diluted with methylene chloride and washed with water and then with brine. The organic layer was concentrated in vacuo to an oil (3.16 g, 80%).

Preparation 5
2,3-Dihydro-benzofuran-7-carboxaldehyde

Step 1: Methyl 2,3-dihydro-benzofuran-7-carboxylate

Methyl benzofuran-7-carboxylate (12 g, 68 mmol) was hydrogenated at 60 psi over 10% Pd/C (2 g) in acetic acid (60 ml) for 18 hr. The mixture was filtered, and the filtrate was concentrated in vacuo to give a pale green oil (12 g, 100%)

Step 2: 2,3-Dihydro-benzofuran-7-methanol

Methyl 2,3-dihydro-benzofuran-7-carboxylate (12 g, 68 mmol) was reduced with LAH (5.14 g, 136 mmol) in THF similar to the above procedures to give the product as a dark oil (8.13 g, 80%).

Step 3: 2.3-Dihydro-benzofuran-7-carboxaldehyde

A solution of 2,3-dihydro-benzofuran-7-methanol (8.13 g, 54.5 mmol) was oxidized using DMSO, oxalyl chloride, and triethyl amine similar to the above procedures to give the product as an oil (7.7 g, 95%).

Preparation 6
2,2-Dimethyl-2,3-dihydro-benzofuran-4-carboxaldehyde

Step 1: Ethyl-3-(2-methylpropenyloxy)benzoate

A mixture of 2-methyl-3-chloropropene (64.2 g, 710 mmol), ethyl 3-hydroxybenzoate (48.21 g, 590 mmol), and potassium carbonate (122.3 g, 890 mmol) in THF (600 ml) and DMF (600 ml) was heated to reflux for 6 hr. The mixture was poured into water (3 L) and extracted with ethyl acetate three times. The ethyl acetate extracts were combined and washed with water and dried with brine. The ethyl acetate extracts were concentrated in vacuo to a yellow oil that was vacuum distilled to a clear oil (112.9 g, 87%).

Step 2: Ethyl 2,2-dimethyl-2,3-dihydro-benzofuran-4-carboxylate

A mixture of ethyl -3-(2-methylpropenyloxy)benzoate (23.6 g, 107 mmol) was stirred with SCX resin (2 g) at 220° C. for 1 hr. The crude product was purified by chromatography on silica gel using methylene chloride as the eluent to give a clear oil (8.7 g, 37%).

Step 3: 2,2-Dimethyl-2,3-dihydro-benzofuran-4-carboxylic acid

Ethyl 2,2-dimethyl-2,3-dihydro-benzofuran-4-carboxylic acid (10 g, 45 mmol) was heated to reflux with sodium hydroxide (16.3 ml of 10N, 163 mmol) in ethanol (50 ml) for 2 hr. The mixture was concentrated in vacuo, diluted with water and made acidic with 12N HCl. The precipitate was filtered and air dried (8.6 g, 100%).

Step 4: 2,2-Dimethyl-2,3-dihydro-benzofuran-4-methanol 2,2-Dimethyl-2,3-dihydro-benzofuran-4-carboxylic acid (8.6 g, 45 mmol) was reduced with LAH (3.41 g, 89 mmol) similar to the above procedures to give the product as a clear oil (7.35 g, 93%).

Step 5: 2,2-Dimethyl-2,3-dihydro-benzofuran-4-carboxaldehyde 2,2-Dimethyl-2,3-dihydro-benzofuran-4-methanol (7.35 g, 41 mmol) was oxidized using DMSO, oxalyl chloride, and triethyl amine similar to the above procedures to give the product as a clear oil (8.87 g, 100%).

Preparation 7
2-Methyl-benzofuran-4-carboxaldehyde
Step 1: Ethyl 2-methyl-benzofuran-4-carboxylate Ozone was bubbled through a solution of ethyl -3-(2-methylpropenyloxy) benzoate (10 g, 45 mmol) at −78° C. for 2 hr until no starting material was present on TLC. The reaction was quenched and the product isolated similar to the above procedures to give the product as a white solid (8.05 g, 87%).

Step 2: 2-Methyl-benzofuran-4-methanol

Ethyl 2-methyl-benzofuran-4-carboxylic acid (5.11 g, 26.6 mmol) was reduced with LAH (2 g, 53 mmol) similar to the above procedures to give the product as a clear oil (3.34 g, 78%).

Step 3: 2-Methyl-benzofuran-4-carboxaldehyde

2-Methyl-benzofuran-4-methanol (3.34 g, 21 mmol) was oxidized using DMSO, oxalyl chloride, and triethyl amine similar to the above procedures to give the product as a clear oil (3.14 g, 93%).

Preparation 8
2,3-Dihydro-1,4-benzodioxin-5-carboxaldehyde 2,3-Dihydroxybenzaldehyde (58 g, 420 mmol) was added to a refluxing mixture of dibromoethane (107.4 g, 570 mmol), sodium hydroxide (35.7 g, 890 mmol) and tetrabutyl ammonium bromide (3 g) in water (50 mL). After heating at reflux for 4 h, the mixture was cooled and the organic layer separated, washed with base, dried over sodium sulfate and concentrated in vacuo. The residue was Kugelrohr distilled at 135° to give the product (48 g, 70%) which solidified on standing (mp 61–62° C.).

Anal. Calc'd: C, 65.85; H, 4.91. Found: C, 65.73; H, 4.86.

Preparation 9
2H-3,4-Dihydro-1,5-benzodioxapin-6-carboxaldehyde 2,3-Dihydroxybenzaldehyde and 1,3-dibromopropane (107.4 g, 570 mmol), sodium hydroxide (35.7 g, 890 mmol) were reacted as described above to give an oil (43%).

Preparation 10
(2H-3,4-Dihydrobenzopyran-5-yl)carboxaldehyde

Step 1: (2H-3,4-Dihydrobenzopyran-5-yl)carboxylic acid

Borane THF complex (55 ml of 1M, 55 mmol) was aded to a solution of ethyl 2-allyl-3-hydroxybenzoate (10.3 g, 50 mmol) in THF at −10° C. The reaction was allowed to warm to room temperature and stirred for 1 hr. A saturated sodium bicarbonate (100 ml) was slowly added then hydrogen peroxide (6 ml) was added dropwise. The mixture was stirred for 30 min, diluted with ethyl acetate (150 ml). The ethyl acetate layer was separated, washed with water, dried with brine, and concentrated in vacuo to a clear oil. This material was dissolved in THF (100 ml) and added slowly to a solution of triphenylphosphine (20.85 g, 79.5 mmol) and diethyl azodicarboxylate (13.84 g, 79.5 mmol) in THF (250 ml). The solution was stirred for 18 hr and then concentrated in vacuo. The residue was distilled in vacuo to give an oil. This oil was purified by chromatography on silica gel using ethyl acetate/methylene chloride (1:1) as the eluent to give a clear oil (11.3 g). This oil was heated to reflux for 2 hr with sodium hydroxide (25 ml of 10N, 250 mmol) and water (50 ml). The reaction was cooled and filtered. The filtrate was made acidic with 12N hydrochloric acid to give a white precipitate (7.96 g, 89%).

Step 2: (2H-3,4-Dihydrobenzopyran-5-yl)methanol (2H,3,4-Dihydrobenzopyran-5-yl)carboxylic acid was reduced with LAH by the above procedures to give the product (97%).

Step 3: (2H-3,4-Dihydrobenzopyran-5-yl)carboxaldehyde (2H-3,4-Dihydrobenzopyran-5-yl)methanol was oxidized using DMSO, oxalyl chloride, and triethyl amine similar to the above procedures to give the product as a clear oil (100%)

Preparation 11
2-Methyl-2,3-dihydrobenzofuran-4-carboxaldehyde

Step 1. Ethyl 2-methyl-2,3-dihydrobenzofuran-4-carboxylate

Ethyl 2-methylbenzofuran-4-carboxylate (10 g), obtained as described in preparation 7, was hydrogenated (60 psi) in acetic acid (100 mL) over 10% Pd/C (2 g) for 24 h. The mixture was filtered through Celite and the filter pad washed well with ethyl acetate. The filtrate was concentrated in vacuo to obtain ethyl 2-methyl-2,3-dihydrobenzofuran-4-carboxylate.

Step 2. 2-Methyl-2,3-dihydrobenzofuran-4-methanol

A solution of ethyl 2-methyl-2,3-dihydrobenzofuran-4-carboxylate (10 g) in THF (100 mL) was stirred as LAH (4.64 g, 122 mmol) was slowly added. The mixture was heated to reflux for 30 min. The mixture was cooled and quenched cautiously with ethyl acetate and then with 1N HCl (150 mL). The mixture was then made acidic with 12N HCl until all the inorganic precipitate dissolved. The organic layer was separated, and the inorganic layer was extracted twice with ethyl acetate. The organic layers were combined, washed twice with brine, and then concentrated in vacuo to provide the desired alcohol.

Step 3. 2-Methyl-2,3-dihydrobenzofuran-4-carboxaldehyde

To a solution of oxalyl chloride(51.6 mL of 2M solution, 103.36 mmol) in dichloromethane(200 mL) at −78° C. under $N_2$ was added dropwise DMSO(9.2 mL, 129.2 mmol) during 10 min. After stirring for 20 min, a solution of alcohol(10.6 g, 64.6 mmol) in dichloromethane( 50 mL) was added dropwise during 10 min. The resulting mixture was stirred for 1 h. Triethylamine(36 mL, 258.4 mmol) was added and allowed to warm to room temperature, and stirred for 0.5 h. The reaction was quenched with water(30 mL), washed with brine, dried over $MgSO_4$, concentrated in vacuo to give a residue. The residue was purified by flash chromatography over silical gel, elution with 6% ethyl acetate in hexane, to give 8.5 g (81%) of the aldehyde as an oil.

Preparation of intermediates of Formula 2

Preparation 12
(trans)-3-(2,3-Dihydrobenzodioxin-5-yl)propenoic acid

A mixture of 2,3-dihydrobenzodioxin-5-carboxaldehyde (Morishima, et al., Eur. Pat. Appl. 309,766, 5 Apr 89) (9.25 g, 56.4 mmol), malonic acid (11.73 g, 112.8 mmol), pyrrolidine (1 mL), and pyridine (25 mL) was heated to reflux for 2 hr, cooled, and then poured into ice water (300 mL). The white precipitate was filtered, washed with 1N HCl, and air dried (9.83 g, 84.6%).

Preparation 13

The following compounds of Formula 2, (a)–(l) were prepared by the general procedure described for the compound of Preparation 12.

(a) (trans) -3-(2,3-Dihydrobenzofuran-4-yl) propenoic acid 2,3-Dihydrobenzofuran-4-carboxaldehyde was subjected to the above procedure to give a pale yellow powder that was recrystallized from isopropanol to give white flakes (95.3%, mp 205–207° C.).

Anal. Calc'd for $C_{11}H_{10}O_3$: C, 69.46; H, 5.30. Found: C, 69.36; H, 5.17.

(b) (trans)-3-(Benzofuran-4-yl)propenoic acid

Benzofuran-4-carboxaldehyde was subjected to the above procedure to give a white powder (83%).

(c) (trans)-3-(1,3-benzodioxol-4-yl)propenoic acid 1,3-Benzodioxole-4-carboxaldehyde was subjected to the above procedure to give a white powder (99%).

(d) (trans)-3-(2,3,4,5-tetrahydrobenzoxepin-6-yl)propenoic acid 2,3,4,5-Tetrahydrobenzoxepin-4-carboxaldehyde was subjected to the above procedure to give this product as a white solid (89%).

(e) (trans)-3-(Benzofuran-7-yl)propenoic acid

Benzofuran-7-carboxaldehyde was subjected to the above procedure to give this product as a white solid (100%).

(f) (trans)-3-(2,3-Dihydro-benzofuran-7-yl)propenoic acid 2,3-Dihydro-benzofuran-7-carboxaldehyde was subjected to the above procedure to give this product as a white solid (100%).

(g) (trans)-3-(2,2-Dimethyl-2,3-dihydro-benzofuran-4-yl)propenoic acid 2,2-Dimethyl-2,3-dihydro-benzofuran-4-carboxaldehyde was subjected to the above procedure to give this product as a white solid (81%).

(h) (trans)-3-(2-Methyl-benzofuran-4-yl) propenoic acid

2-Methyl-benzofuran-4-carboxaldehyde was subjected to the above procedure to give this product as a white solid (97%).

(i) (trans)-3-(2,3-Dihydro-1,4-benzodioxin-5-yl)propenoic acid 2,3-Dihydro-1,4-benzodioxan-5-carboxaldehyde was reacted with malonic acid as described above to give a white solid (90%).

(j) (trans)-3-(2H-3,4-Dihydro-1,5-benzodioxapin-6-yl)propenoic acid 2H-3,4-Dihydro-1,5-benzodioxapin-6-carboxaldehyde was reacted with malonic acid as described above to give a white solid (74%).

(k) (trans)-3-(2H-2,3-Dihydrobenzopyran-4-yl)propenoic acid (2H-2,3-Dihydrobenzopyran-4-yl)carboxaldehyde was reacted with malonic acid by the above procedures to give the white solid (98%).

(l) (trans)-3-(2-Methyl-2,3-dihydrobenzofuran-4-yl)propenoic acid

2-Methyl-2,3-dihydrobenzofuran-4-carboxaldehyde was reacted with malonic acid by the above procedures to give the desired acid (92%).

Preparation of intermediates of Formula 3

Preparation 14

(trans)-N-Methoxy-N-methyl-3-(2,3-Dihydrobenzodioxin-5-yl)propenamide

A mixture of (trans)-3-(2,3-dihydrobenzodioxin-5-yl)propenoic acid (9.83 g, 47.7 mmol), thionyl chloride (20 mL), and $CH_2Cl_2$ (75 mL) was heated to reflux for 1 hr, and then concentrated in vacuo to give a yellow-green solid. This material was dissolved in ethyl acetate (75 mL), and a solution of N,O-dimethylhydroxylamine hydrochloride (9.5 g) in saturated $Na_2CO_3$ (100 mL) was added with stirring. The mixture was stirred for 90 min and then diluted with water and ethyl acetate. The ethyl acetate layer was separated and washed twice with water and twice with saturated $Na_2CO_3$. The ethyl acetate layer was concentrated in vacuo to give a brown oil. This crude product was chromatographed on silica gel using 1:1 ethyl acetate/methylene chloride as the eluent to give a clear oil that crystallized upon standing (11.1 g, 93.1%).

Preparation 15

The following compounds of Formula 3, (a)–(k) were prepared by the general procedure described for the compound of Preparation 14.

(a) (trans)-N-Methoxy-N-methyl-3-(benzofuran-4-yl)propenamide (trans)-3-(Benzofuran-4-yl)-propenoic acid was subjected to the above procedure to give an oil (97.7%).

(b) (trans)-N-Methoxy-N-methyl-3-(2,3,4,5-tetrahydrobenzoxepin-6-yl)propenamide (trans)-3-(2,3,4,5-Tetrahydrobenzoxepin-6-yl)-propenoic acid was subjected to the above procedures to give this product (88.6%).

(c) (trans)-N-Methoxy-N-methyl-3-(benzofuran-7-yl)propenamide (trans)-3-(Benzofuran-7-yl)propenoic acid was subjected to the above procedures to give this product (90%).

(d) (trans)-N-Methoxy-N-methyl-3-(2,3-dihydro-benzofuran-7-yl)propenamide (trans)-3-(2,3-Dihydro-benzofuran-7-yl)propenoic acid was subjected to the above procedures to give this product (68%).

(e) (trans)-N-Methoxy-N-methyl-3-(2,2-dimethyl-2,3-dihydro-benzofuran-4-yl)propenamide (trans)-3-(2,2-Dimethyl-2,3-dihydro-benzofuran-4-yl)propenoic acid was subjected to the above procedures to give this product (92%).

(f) (trans)-N-Methoxy-N-methyl-3-(2-methyl-benzofuran-4-yl) propenamide (trans)-3-(2-Methyl-benzofuran-4-yl)propenoic acid was subjected to the above procedures to give this product (100%).

(g) (trans)-N-Methoxy-N-methyl-3-(2,3-dihydro-1,4-benzodioxin-5-yl)propenamide (trans)-3-(2,3-Dihydro-1,4-benzodioxan-5-yl)propenoic acid was subjected to the above procedures to give this product (85%).

(h) (trans)-N-Methoxy-N-methyl-3-(2H-3,4-dihydro-1,5-benzodioxapin-6-yl)propenamide (trans)-2H-3-(3,4-Dihydro-1,5-benzodioxapin-6-yl)propenoic acid was subjected to the above procedures to give this product (86%).

(i) (trans)-N-Methoxy-N-methyl-3-(2H-2,3-dihydrobenzopyran-4-yl)propenamide (trans)-3-(2H-2,3-Dihydrobenzopyran-4-yl)propenoic acid was subjected to the above procedures to give this product (quantitative yield).

(j) (trans)-N-Methoxy-N-methyl-3-(1,3-benzodioxol-4-yl)-propenamide 1,3-Benzodioxole-4-carboxaldehyde was subjected to the above procedure to give a red oil (100%).

(k) (trans)-N-Methoxy-N-methyl-3-(2,3-dihydrobenzofuran-4-yl)propenamide

Diethyl (N-methoxy-N-methyl-carbamoylmethyl) phosphonate (4.0 g, 16.7 mmol) was added dropwise to a suspension of sodium hydride (671 mg, 60% dispersion in mineral oil, 16.7 mmol) in THF (75 mL) at 0° C. A solution of 2,3-dihydrobenzofuran-4-carboxaldehyde (3.0 g, 15.2 mmol) in THF (25 mL) was added dropwise. The resulting suspension was allowed to warm to room temperature. After 18 h, water (60 mL) was added and the solution was extracted three times with ethyl acetate. The organic extracts were combined, washed with water and brine, dried over $K_2CO_3$, and concentrated to give a pale red oil, 3.5 g (100%).

Preparation of intermediates of Formula 4

Preparation 16

(+)-(trans)-2-(2,3-Dihydrobenzofuran-4-yl)cyclopropanecarboxaldehyde

Step 1: (±)-(trans)-N-Methoxy-N-methyl-2-(2,3-dihydrobenzofuran-4-yl)cyclopropanecarboxamide Trimethylsulfoxonium iodide (9.9 g, 45 mmol) was added in small portions to a suspension of sodium hydride (1.8 g, 45 mmol) in DMF (120 mL). After the foaming had subsided (10 min), a solution of (trans)-N-methoxy-N-methyl-3-(2,3-dihydrobenzofuran-4-yl)propenamide (3.5 g, 15 mmol) in DMF (60 mL) was added dropwise, with the temperature maintained between 35–40° C. The mixture was stirred for 3 h at room temperature. Saturated $NH_4Cl$ (50 mL) was added dropwise and the mixture was extracted three times with ethyl acetate. The organic extracts were combined, washed with $H_2O$ and brine, dried over $K_2CO_3$, and concentrated in vacuo to give a white wax (3.7 g, 100%).

Step 2: (±)-(trans)-2-(2,3-Dihydrobenzofuran-4-yl)cyclopropane-carboxaldehyde

A solution of (±)-(trans)-N-methoxy-N-methyl-2-(2,3-dihydrobenzofuran-4-yl)cyclopropanecarboxamide (3.7 g, 15 mmol) in THF (10 mL) was added dropwise to a rapidly stirred suspension of LAH (683 mg, 18 mmol) in THF (50 mL) at –45° C, maintaining the temperature below –40° C. throughout. The cooling bath was removed, the reaction was allowed to warm to 5° C., and then the reaction was immediately recooled to –45° C. Potassium hydrogen sulfate (3.4 g, 25.5 mmol) in $H_2O$ (50 mL) was cautiously added dropwise, the temperature maintained below –30° C. throughout. The cooling bath was removed and the suspension was stirred at room temperature for 30 min. The mixture was filtered through Celite and the filter cake was washed with ether. The combined filtrates were then washed with cold 1N HCl, 1N NaOH, and brine. The filtrates were dried over $MgSO_4$, and concentrated in vacuo to give a clear oil (2.6 g, 99%).

Preparation 17

The following compounds of Formula 4 (a)–(k) were prepared by the general procedure described for the compound of Preparation 16.

(a) (±)-(trans)-2-(Benzofuran-4-yl)cyclopropanecarboxaldehyde (trans)-N-Methoxy-N-methyl-3-(benzofuran-4-yl)propenamide was subjected to the above procedure to give an oil (93.3%).

(b) (±)-(trans)-2-(1,3-Benzodioxol-4-yl) cyclopropanecarboxaldehyde (trans)-N-Methoxy-N-methyl-3-(1,3-benzodioxol-4-yl)propenamide was subjected to the above procedure to give a clear oil (100%).

(c) (±)-(trans)-2-(2,3-Dihydrobenzodioxan-5-yl)cyclopropanecarboxaldehyde (trans)-N-Methoxy-N-methyl-3-(2,3-dihydrobenzodioxan-5-yl)propenamide was subjected to the above procedure to give an orange oil (90%).

(d) (±)-(trans)-2-(2,3,4,5-Tetrahydrobenzoxepin-6-yl)cyclopropanecarboxaldehyde (trans)-N-Methoxy-N-methyl-3-(2,3,4,5-tetrahydrobenzoxepin-6-yl)propenamide was subjected to the above procedures to give this product (36%).

(e) (±)-(trans)-2-(Benzofuran-7-yl)cyclopropanecarboxaldehyde (trans)-N-Methoxy-N-methyl-3-(benzofuran-7-yl)propenamide was subjected to the above procedures to give this product (67%).

(f) (±)-(trans)-2-(2,3-Dihydro-benzofuran-7-yl)cyclopropanecarboxaldehyde (trans)-N-Methoxy-N-methyl-3-(2,3-dihydro-benzofuran-7-yl)propenamide was subjected to the above procedures to give this product (55%).

(g) (±)-(trans)-2-(2,2-Dimethyl-2,3-dihydro-benzofuran-4-yl)cyclopropanecarboxaldehyde (trans)-N-Methoxy-N-methyl-3-(2,2-dimethyl-2,3-dihydro-benzofuran-4-yl)propenamide was subjected to the above procedures to give this product (64%).

(h) (±)-(trans)-2-(2-Methyl-benzofuran-4-yl)cyclopropanecarboxaldehyde (trans)-N-Methoxy-N-methyl-3-(2-methyl-benzofuran-4-yl)propenamide was subjected to the above procedures to give this product (100%).

(i) (trans)-2-(2,3-dihydro-1,4-benzodioxan-5-yl)cyclopropanecarboxaldehyde (trans)-N-Methoxy-N-methyl-3-(2,3-dihydro-1,4-benzodioxan-5-yl)propenamide was subjected to the above procedures to give this product (79%).

(j) (trans)-2-(2H-3,4-dihydro-1,5-benzodioxapin-6-yl)cyclopropanecarboxaldehyde (trans)-N-Methoxy-M-methyl-3-(2H-3,4-dihydro-1,5-benzodioxapin-6-yl)propenamide was subjected to the above procedures to give an oil (55%).

(k) (±)-(trans)-2-(2H-2,3-Dihydrobenzopyran-4-yl)cyclopropanecarboxaldehyde (trans)-N-Methoxy-N-methyl-3-(2H-2,3-dihydrobenzopyran-4-yl)propenamide was subjected to the above procedure to give this product (86%).

Preparation 18

(−)-(trans)-2-(2,3-Dihydrobenzofuran-4-yl)cyclopropanecarboxaldehyde

Step 1: (−)-(trans)-N-[3-(2,3-Dihydrobenzofuran-4-yl)-propenoyl]-2,10-camphorsultam To a solution of (−)-2,10-camphorsultam (8.15 g, 37.9 mmol) in 50 mL toluene at 0° C. was added sodium hydride (1.67 g, 41.7 mmol). After stirring for 0.33 h at 0° C. and 0.5 h at 20° C. and recooling to 0° C., a solution of 3-(2,3-dihydrobenzofuran-4-yl)-2-propenoyl chloride (37.9 mmol), prepared in situ from the corresponding acid and thionyl chloride (75 mL), in toluene (50 mL), was added dropwise. After stirring for 18 h at 20° C., the mixture was diluted with ethyl acetate and washed with water, 1N HCl, and 1N NaOH. The organic solution was dried and concentrated in vacuo to give 15.8 g of crude product. Recrystallization form ethanol-methanol (600 mL, 1:1) gave the product (13.5 g, 92%, mp 199.5–200° C.).

Step 2: (–)-N-[[(trans)-2-(2,3-Dihydrobenzofuran-4-yl)-cyclopropyl]-carbonyl]-2,10-camphorsultam 1-Methyl-3-nitro-1-nitrosoguanidine (23.88 g 163 mmol) was added in portions to a mixture of 10N sodium hydroxide (60 mL) and ether (200 mL) at 0° C. The mixture was shaken vigorously for 0.25 h and the ether layer carefully decanted into a solution of (–)-N-[3-(2,3-dihydrobenzofuran-4-yl)-2-propenoyl]-2,10-camphorsultam (9.67 g, 25 mmol) and palladium acetate (35 mg) in methylene chloride (200 mL). After stirring for 18 h, acetic acid (5 mL) was added to the reaction and the mixture stirred for 0.5 h. The mixture was washed with 1N HCl, 1N NaOH and brine. The solution was dried, concentrated in vacuo and the residue crystallized twice from ethanol to give the product (6.67 g, 66.5%, mp 157–159° C.).

Step 3: (–)-(trans)-2-(2,3-Dihydrobenzofuran-4-yl) cyclopropane-methanol

A solution of (–)-N-[(trans)-2-(2,3-dihydrobenzofuran-4-yl)cyclopropanecarbonyl]-2,10-camphorsultam (4.3 g, 10.7 mmol) in THF (50 mL) was added dropwise to a mixture of LAH (0.81 g, 21.4 mmol) in THF (50 mL) at –45° C. The mixture was stirred for 2 hr while it warmed to 10° C. The mixture was recooled to –40° C. and hydrolyzed by the addition of saturated $KHSO_4$ (20 mL). The mixture was stirred at room temperature for 30 minutes and filtered. The precipitate was washed twice with acetone. The combined filtrate and acetone washes were concentrated in vacuo. The gummy residue was dissolved in ether, washed with 1N NaOH and 1N HCl, and then dried in vacuo to give the product (2.0 g, 98.4%).

Step 4: (–)-(trans)-2-(2,3-Dihydrobenzofuran-4-yl) cyclopropanecarboxaldehyde

DMSO (1.6 g, 21 mmol) was added to oxalyl chloride in $CH_2Cl_2$ (7.4 mL of 2M solution, 14.8 mmole) at –78° C. The (–)-(trans)-2-(2,3-dihydrobenzofuran-4-yl)-cyclopropylmethanol (2.0 g, 10.5 mmol) in $CH_2Cl_2$ (15 mL) was added. The mixture was stirred for 20 min and then triethylamine (4.24 g, 42 mmol) was added. The mixture was warmed to room temperature and stirred for 30 min. The mixture was diluted with $CH_2Cl_2$ and washed with water, 1N HCl), and then 1N NaOH. The organic layer was dried and concentrated in vacuo to give the aldehyde product (1.98 g, 100%).

Preparation 19
(–)-(trams)-2-(2,3-Dihydro-1,4-benzodioxan-5-yl) cyclopropanecarboxaldehyde Step 1: (–)-(trans)-N-[3-(2,3-Dihydro-1,4-benzodioxan-5-yl)propenoyl]-2,10-camphorsultam (trans)-3-(2,3-Dihydro-1,4-benzodioxan-5-yl)propenoic acid was subjected to the above procedure to give (88%, mp 187–188° C.).

Step 2: (–)-N-(trans)-[[2-(2,3-Dihydro-1,4-benzodioxan-5-yl)cycloprop-1-yl]carbonyl]-2,10-camphorsultam (–)-(trans)-N-[3-(2,3-Dihydro-1,4-benzodioxan-5-yl) propenoyl]-2,10-camphorsultam was subjected to the above procedure to give (84%, mp 214–215° C., $[\alpha]_D^{25}$=–138.9).

Step 3: (–)-(trans)-2-(2,3-Dihydro-1,4-benzodioxan-5-yl)-1-cyclopropanemethanol (–)-N-(trans)-[[3-(2,3-Dihydro-1,4-benzodioxan-5-yl) cyclopropyl]carbonyl]-2,10-camphorsultam was reduced with LAH as described above to give the product as an oil (100%)

Step 4: (–)-(trans)-2-(2,3-Dihydro-1,4-benzodioxan-5-yl)-1-cyclopropanecarboxaldehyde (–)-(trans)-2-(2,3-Dihydro-1,4-benzodioxan-5-yl)-1-cyclopropanemethanol was oxidized under as described above to give the aldehyde as an oil (100%) which was immediately used in the next reaction.

Preparation 20
(+)-(trans)-2-(2-Methyl-2,3-dihydrobenzofuran-4-yl) cyclopropane-carboxaldehyde and (–)-(trans)-2-(2-Methyl-2,3-dihydrobenzofuran-4-yl)cyclopropane-carboxaldehyde Step 1: (trans)-N-[3-(2-Methyl-2,3-dihydrobenzofuran-4-yl)propenoyl]-2.10-camphorsultam (trans)-N-[3-(2-Methyl-2,3-dihydrobenzofuran-4-yl) propenoic acid was subjected to the above procedure to give the desired sultam (95% yield for two steps).

Step 2: N-(trans)-[[2-(2-Methyl-2 3-dihydrobenzofuran-4-yl)cycloprop-1-yl]carbonyl]-2,10-camphorsultam (trans)-N-[3-(2-Methyl-2,3-dihydrobenzofuran-4-yl) propenoyl]-2,10-camphorsultam was subjected to the above procedure to give the desired cyclopropane derivative (61%).

Step 3: (trans)-2-(2-Methyl-2,3-dihydrobenzofuran-4-yl)-1-cyclopropanemethanol

N-(trans)-[[2-(2-Methyl-2,3-dihydrobenzofuran-4-yl) cycloprop-1-yl]carbonyl]-2,10-camphorsultam was reduced with LAH as described above to give the desired alcohol as a mixture of diastereomers (96%). The mixture of diastereomeric alcohols was separated by chiral HPLC (Chiracel OD, iPrOH/hexanes) to give both (+)-(trans)-2-(2-Methyl-2,3-dihydrobenzofuran-4-yl)-1-cyclopropanemethanol and (–)-(trans)-2-(2-Methyl-2,3-dihydrobenzofuran-4-yl)-1-cyclopropanemethanol.

Step 4: (+)-(trans)-2-(2-Methyl-2,3-dihydrobenzofuran-4-yl)-1-cyclopropanecarboxaldehyde and (–)-(trans)-2-(2-Methyl-2,3-dihydrobenzofuran-4-yl)-1-cyclopropanecarboxaldehyde The separated (+)-(trans)-2-(2-Methyl-2,3-dihydrobenzofuran-4-yl)-1-cyclopropanemethanol and the separated (–)-(trans)-2-(2-Methyl-2,3-dihydrobenzofuran-4-yl)-1-cyclopropanemethanol were separately oxidized as described above to give the corresponding desired aldehydes (98% and 97% yield, respectively).

Preparation of intermediates of Formula 5

Preparation 21
2,2-Difluoro-3-(2-methyl-4-benzofuranyl) cyclopropanemethanol, O-acetate Step 1. (trans)-3-(2-Methyl-4-benzofuranyl)-2-propen-1-ol A solution of (trans)-3-(2-methyl-4-benzofuranyl)-2-propenoic acid (2.53 g, 10.9 mmol) in 30 mL anhydrous THF was added slowly to a mixture of sodium borohydride (592 mg, 15.6 mmol) in 15 mL of anhydrous THF at RT. Once the evolution of hydrogen had ceased, the reaction mixture was cooled to 0° C. and a solution of $I_2$ (1.72 g, 6.76 mmol) in 15 mL THF was added. The reaction mixture was stirred at 0° C. for 1 h, allowed to warm to RT and stirred at RT for an additional 3 h. The reaction was then quenched with 3N HCl and the aqueous layer extracted with ether. The combined organic layers were washed with 3N NaOH and brine, then dried over $MgSO_4$ and concentrated in vacuo. Purification on silica gel (ethyl acetate/hexanes) afforded a mixture of the allylic alcohol and the saturated alcohol (10:1) in a combined yield of 46%. The mixture was carried through the next step.

Step 2. (trans)-3-(2-Methyl-4-benzofuranyl)-2-propen-1-ol, O-acetate

Acetic anhydride (1.20 mL, 12.6 mmol) was added to a solution of the mixture containing (trans)-3-(2-methyl-4-benzofuranyl)-2-propen-1-ol (as obtained in the previous step) in 10 mL pyridine at −5° C. The reaction mixture was stirred at RT for 20 h then diluted with ether. The crude mixture was washed with 1N HCl, saturated $NaHCO_3$, water, and brine then dried over $MgSO_4$, filtered and dried in vacuo. Purification on silica gel (ethyl acetate/hexanes) afforded a mixture of the allylic acetate and the saturated acetate in a combined yield of 73%.

Step 3. 2,2-Difluoro-3-(2-methyl-4-benzofuranyl)-cyclopropanemethanol, O-acetate To a refluxing solution of (trans)-3-(2-methyl-4-benzofuranyl)-2-propen-1-ol, O-acetate (0.1 g, 4.35 mmol) in 10 ml of diglyme was slowly added a solution of $ClF_2CCOONa$ (5.0 g, 32.6 mmo) in 10 ml of diglyme. The reaction solution was stirring at 165° C. for 1.5 h, cooled to room temperature and filtered through Celite. The filtrate was diluted with ether and washed with large amounts of water. The aqueous layer was extracted with ether. The combined organic layers were washed with water and brine solution and dried over $MgSO_4$. Solvent was removed in vacuo. Purification on silica gel (ethyl acetate/hexanes) afforded 2,2-difluoro- 3-(2-methyl-4-benzofuranyl) cyclopropanemethanol, O-acetate (560 mg, 56%) as a colorless liquid. $^1$H NMR (300 MHz, $CDCl_3$) δ 2.12 (s, 3H), 2.25–2.36 (m,1H), 2.46 (s, 3H), 2.76–2.88 (m,1H), 4.27–4.45 (m, 2H), 6.47 (s, 1H), 7.00 (d, 1H, J=7.5 Hz), 7.15 (t, 1H, J=7.5 Hz), 7.33 (d, 1H, J=7.5 Hz). $^{13}$C NMR (75 MHz, $CDCl_3$) δ 14.4, 18.4, 27.8 (t, J=10.4 Hz), 29.8 (t, J=10.4 Hz), 61.2, 101.2, 110.4, 113.5 (t, J=286.7 Hz), 121.7, 123.3, 124.3, 129.7, 154.8, 156.2, 171.1.

Preparation of intermediates of Formula 7

Preparation 22
(±)-(trans)-2-(2,3-dihydrobenzofuran-4-yl)cyclopropane-methanamine A solution of (±)-(trans)-2-(2,3-dihydrobenzofuran-4-yl)-cyclopropane-carboxaldehyde (2.6 g, 15 mmol), hydroxylamine hydrochloride (3.13 g, 45 mmol), ethanol (60 mL), water (40 mL), and 10N NaOH (4.5 mL, 45 mmol) was heated to reflux for 4 h. The solution was cooled to room temperature, diluted with water and ethyl acetate. The ethyl acetate layer was separated and washed sequentially with $H_2O$ and brine. The ethyl acetate extract was dried over $K_2CO_3$ and concentrated in vacuo. The residue was dissolved in THF (50 mL) and added dropwise to a −45° C. suspension of LAH (1.06 g, 28 mmol) in THF (100 mL), maintaining the temperature below −40° C. The reaction was warmed to room temperature and stirred for 2 h. The reaction was recooled to −45° C., and 1N HCl (50 mL) was cautiously added dropwise. The cooling bath was removed and the suspension was stirred at room temperature for 30 min. The resulting paste was then diluted with ethyl ether and extracted with 1N HCl. The acid extracts were combined, washed with ethyl ether, made basic with 50% NaOH, and extracted with dichloromethane. The dichloromethane extracts were combined, washed with brine, dried over $K_2CO_3$, and concentrated in vacuo to give a clear oil (900 mg, 40%).

Preparation 23

The following compounds of Formula 7, (a)–(m) were prepared by the general procedure described for the compound in Preparation 22.

(a) (±)-(trans)-2-(Benzofuran-4-yl)-cyclopropanemethanamine (±)-(trans)-2-(Benzofuran-4-yl) cyclopropanecarboxaldehyde was subjected to the above procedure to give an oil (73.5%).

(b) (±)-(trans)-2-(1,3-Benzodioxol-4-yl) cyclopropanemethanamine (±)-(trans)-2-(1,3-Benzodioxol-4-yl) cyclopropanecarboxaldehyde was reacted by the above procedure to give a red oil (61%).

(c) (±)-(trans)-2-(2,3-Dihydrobenzodioxan-5-yl) cyclopropane-methanamine (±)-(trans)-2-(2,3-Dihydrobenzodioxan-5-yl) cyclopropane-carboxaldehyde was reacted by the above procedure to give an orange oil (91.1%).

(d) (±)-(trans)-2-(2,3,4,5-tetrahydrobenzoxepin-6-yl) cyclopropane-methanamine (±)-(trans)-2-(2,3,4,5-tetrahydrobenzoxepin-6-yl) cyclopropane-carboxaldehyde was reacted by the above procedures to give this product (50%).

(e) (±)-(trans)-2-(Benzofuran-7-yl) cyclopropanemethanamine (±)-(trans)-2-(Benzofuran-7-yl) cyclopropanecarboxaldehyde was reacted by the above procedures to give this product (66%).

(f) (±)-(trans)-2-(2,3-Dihydro-benzofuran-7-yl) cyclopropane-methanamine (±)-(trans)-2-(2,3-Dihydro-benzofuran-7-yl) cyclopropanecarboxaldehyde was reacted by the above procedures to give this product (87%).

(g) (±)-(trans -2-(2,2-Dimethyl-2,3-dihydro-benzofuran-4-yl)cyclopropanemethanamine (±)-(trans)-2-(2,2-Dimethyl-2,3-dihydro-benzofuran-4-yl)cyclopropane-carboxaldehyde was reacted by the above procedures to give this product (60%).

(h) (±)-(trans)-2-(2-Methyl-benzofuran-4-yl) cyclopropanemethanamine (±)-(trans)-2-(2-Methyl-benzofuran-4-yl) cyclopropanecarboxaldehyde was reacted by the above procedures to give this product (63%).

(i) (trans)-2-(2,3-Dihydro-1,4-benzodioxan-5-yl) cyclopropanemethanamine (trans)-2-(2,3-dihydro-1,4-benzodioxan-5-yl) cyclopropanecarboxaldehyde was reacted by the above procedures to give the amine (67%) which was converted to the furmarate (mp 183–184° C.).

(j) (trans)-2-(2H-3,4-Dihydro-1,5-benzodioxapin-6-yl) cyclopropanemethanamine trans-(trans)-2-(2H-3,4-Dihydro-1,5-benzodioxapin-6-yl)-cyclopropanecarboxaldehyde was reacted by the above procedures to give the amine which was converted to the fumarate (65%, mp 152–153° C.).

Anal. Calc'd for $0.3H_2O$: C, 59.92; H, 6.39; N 4.11. Found: C, 50.78; H, 6.33; N, 4.01.

(k) (±)-(trans)-2-(2H-2,3-Dihydrobenzopyran-4-yl) cyclopropanemethanamine (±)-(trans)-2-(2H-2,3-Dihydrobenzopyran-4-yl) cyclopropanecarboxaldehyde was reacted by the above procedure to give this product (42%).

(l) (−)-(trans)-2-(2-Methyl-2,3-dihydrobenzofuran-4-yl) cyclopropanemethanamine (−)-(trans)-2-(2-Methyl-2,3-dihydrobenzofuran-4-yl) cyclopropanecarboxaldehyde was subjected to the above procedure to give the desired amine (71%).

(m) (+)-(trans)-2-(2-Methyl-2 3-dihydrobenzofuran-4-yl) cyclopropanemethanamine (+)-(trans)-2-(2-Methyl-2,3-dihydrobenzofuran-4-yl) cyclopropanecarboxaldehyde was subjected to the above procedure to give the desired amine (59%).

Preparation 24
(−)-(trans)-2-(2,3-Dihydrobenzofuran-4-yl) cyclopropanemethanamine A mixture of (−)-(trans)-2-(2,3-dihydrobenzofuran-4-yl) cyclopropanecarboxaldehyde (1.98 g, 10.5 mmol), hydroxylamine hydrochloride (2.29 g, 33 mmol), and 30% NaOH (3.5 mL, 35 mmol), in 5:1 ethanol/water (50 mL) was heated on a steam bath for 2 h. The solution was concentrated in vacuo, and the residue mixed with water. The mixture was extracted with $CH_2Cl_2$. The organic extracts were dried and concentrated in vacuo to give a solid which NMR analysis showed to be a mixture of the cis and trans oximes. This material was dissolved in THF (20 mL) and added to solution of alane in THF [prepared from LAH (1.14 g, 30 mmol) and $H_2SO_4$ (1.47 g, 15 mmol) at 0° C.]. The reaction was stirred for 18 h, and quenched successively with water (1.15 mL), 15% NaOH (1.15 mL), and then water (3.45 mL). The mixture was filtered and the filtrate was concentrated in vacuo. The residue was mixed with ether and washed with water and then 1N HCl. The acid washes were made basic and extracted with $CH_2Cl_2$. The extracts were dried and concentrated in vacuo to give the amine product (1.4 g, 70.5%). The amine was converted to the fumarate salt in ethanol (mp: 197–198° C.).

Anal. Calc'd for $C_{12}H_{15}NO·C_4H_4O_4$: C, 62.94; H, 6.27; N, 4.59. Found: C, 62.87; H, 6.31; N, 4.52.

Preparation 25
(−)-(trans)-2-(1,3-Benzodioxol-4-yl) cyclopropanemethanamine (−)-(trans)-2-(1,3-Benzodioxol-4-yl) cyclopropanecarboxaldehyde was subjected to the above general procedure described in Preparation 24 to give a beige solid (52.6%).

Preparation 26
(+)-trans-2-[(2,3-Dihydro-1,4-benzodioxin-5-yl)cycloprop-1-yl]methylamine Step 1: (−)-(trans)-2-(2,3-Dihydro-1,4-benzodioxin-5-yl)-1-cyclopropanecarboxaldehyde oxime (−)-(trans)-2-(2,3-Dihydro-1,4-benzodioxin-5-yl)-1-cyclopropanecarboxaldehyde was reacted with hydroxyl amine as described above to give the oxime as a mixture of isomers.

Step 2: (+)-trans-2-[(2,3-dihydro-1,4-benzodioxin-5-yl) cycloprop-1-yl]methylamine The above oxime was reduced with alane as described above to give the amine which was converted to the fumarate (80%, mp 173–174° C. for fumarate, $[\alpha]_D^{25}$=6.15).

Anal. Calc'd for $0.5H_2O$: C, 58.36; H, 6.10; N 4.24. Found: C, 58.36; H, 6.09; N, 4.24.

Preparation 27
2,2-Difluoro-3-(2-methyl-4-benzofuranyl) cyclopropanemethanamine

Step 1. 2,2-Difluoro-3-(2-methyl-4-benzofuranyl) cyclopropanemethanol

To a stirred solution of 2,2-difluoro-3-(2-methyl-4-benzofuranyl)-cyclopropanemethanol, O-acetate (560 mg, 2.0 mmol) in MeOH/THF (10 ml, 3/1) was added powdered KOH (560 mg, 10.0 mmol). The resulting solution was stirred at RT for 2 h. Solvent was removed in vacuo. The residue was diluted with ether and water. The aqueous layer was extracted with ether and the combined organic layers were washed with saturated $NaHCO_3$, water and brine solution. Solvent was removed in vacuo. Purification on silica gel (ethyl acetate/hexanes) afforded 2,2-difluoro-3-(2-methyl-4-benzofuranyl)cyclopropanemethanol (420 mg, 88%) as a white solid.$^1$H NMR (300 MHz, $CDCl_3$) δ 1.67 (bs, 1H), 2.19–2.31 (m,1H), 2.46 (s, 3H), 2.73–2.80 (m,1H), 3.95–3.98 (m, 2H), 6.51 (s, 1H), 7.02 (d, 1H, J=7.5Hz), 7.15 (t, 1H, J=7.5 Hz), 7.32, (d, 1H, J=7.5 Hz). $^{13}$C NMR (75 MHz, $CDCl_3$) δ 14.4, 29.3 (t, J=10.4 Hz), 31.3 (t, J=10.4 Hz), 60.1, 101.3, 110.2, 114.1 (t, J=286.7 Hz), 121.7, 123.3, 124.7, 129.8, 154.7, 156.1.

Step 2. 4-[2-(Azidomethyl)-3,3-difluorocyclopranyl]-2-methylbenzofuran

Triethylamine (916 ml, 6.55 mmol) followed by $CH_3SO_2Cl$ (355 ml, 4.59 mmol) were added to a solution of 2,2-difluoro-3-(2-methyl-4-benzofuranyl) cyclopropanemethanol (390 mg, 1.64 mmol) in 15 ml of $CH_2Cl_2$. The reaction was stirred at RT for 0.5 h and diluted with $CH_2Cl_2$. The organic layer was washed with water and $NaHCO_3$ and dried over anhydrous $K_2CO_3$. Removal of solvent in vacuo afforded crude mesylate, which was used immediately in the next step. A solution of the mesylate and $NaN_3$ (213 mg, 3.27 mmol) in 12 ml of $CH_2Cl_2$ was heated to 70° C. for 2.5 h. The resulting solution was cooled to RT and diluted with EtOAc and water. The aqueous layer was extracted with EtOAc. The combined organic layers were washed with water and dried over $MgSO_4$. Removal of solvent in vacuo afforded 4-[2-(azidomethyl)-3,3-difluorocyclopranyl]-2-methylbenzofuran (422 mg, 98%). $^1$H NMR (300 MHz, $CDCl_3$) δ 2.16–2.28 (m, 1H), 2.47 (s, 3H), 2.74–2.81 (m, 1H), 3.52–3.70 (m, 2H), 6.49 (s, 1H), 7.02 (d, 1H, J=7.5 Hz), 7.16 (t, 1 H, J=7.5 Hz), 7.34 (d, 1H, J=7.5 Hz).

Step 3. 2,2-Difluoro-3-(2-methyl-4-benzofuranyl) cyclopropanemethanamine

A solution of 4-[2-(azidomethyl)-3,3-difluorocyclopranyl]-2-methylbenzofuran (203 mg, 0.78 mmol) in 4 ml of THF was added dropwise to a solution of LAH (1.0M solution in THF, 1.56 ml. 1.56 mmol) at −30° C. The resulting solution was allowed to warm up to RT and stirred at RT for 3 h. A solution of $KHSO_4$ (130 mg, 0.96 mmol) in 1 ml of water was added to the reaction at −30° C. After stirring at RT for 20 min, the reaction solution was filtered and the filtrate was diluted with $CH_2Cl_2$. The solution was adjusted to pH=10 by addition of $NH_4OH$. The aqueous layer was extracted with $CH_2Cl_2$. The combined organic layers were washed with brine and dried over $K_2CO_3$. Solvent was removed in vacuo to afford 2,2-difluoro-3-(2-methyl-4-benzofuranyl) cyclopropanemethanamine (182 mg, 99%) as colorless liquid.

EXAMPLES

The following examples illustrate the preparation of the compounds of the invention by following the general procedures described above.

Example 1
(±)-(trans)-N-[[2-(2,3-Dihydrofuran-4-yl)cycloprop-1-yl]methyl]acetamide Acetic anhydride (0.14 mL, 1.8 mmol) was added dropwise to a stirred solution of (±)-(trans)-2-(2,3-dihydrobenzofuran-4-yl)-cyclopropanemethanamine (300 mg, 1.6 mmol) and triethylamine (0.67 mL, 4.8 mmol) in dry dichloromethane (15 mL) at 0° C. The resulting suspension was warmed to room temperature and stirred for 18 h. The mixture was concentrated in vacuo and the residue was purified by flash chromatography (silica gel, CH₂Cl₂ then 2% EtOAc/CH₂Cl₂) to afford 200 mg (54%) of a clear oil. IR (NaCl Film): 3287, 2923, 1651, 1553, 1459 cm$^{-1}$.

Anal. Calc'd for $C_{14}H_{17}NO_2 \cdot 0.3H_2O$: C, 71.04; H, 7.50; N, 5.92. Found: C, 70.79; H, 7.41; N, 5.58.

Example 2
(−)-(trans)-N-[[2-(2,3-Dihydrobenzofuran-4-yl)cycloprop-1-yl]methyl]propanamide This compound was prepared similar to the above procedure using propionyl chloride and (−)-(trans)-2-(2,3-dihydrobenzofuran-4-yl)-cyclopropanemethanamine to give an oil that solidified upon standing to an off-white solid (61%, mp: 71–72° C.).

IR (NaCl Film): 3298, 1645, 1548, 1459, 1235 cm$^{-1}$.

$[\alpha]_D^{25}$: −17.3°

Anal. Calc'd for $C_{15}H_{19}NO_2$: C, 73.44; H, 7.87; N, 5.71. Found: C, 73.28; H, 7.68; N, 5.58.

The following compounds of Formula I were prepared by these general methods:

TABLE 2

Physical Data for Compounds of Formula I

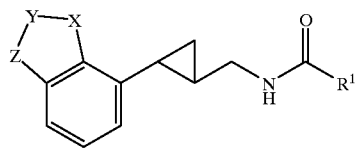

(I)

| Ex. | X—Y—Z | R¹ | $[\alpha]_D^{25}$ | % C (Calc/Found) | % H (Calc/Found) | % N (Calc/Found) | Emperical Formula | mp ° C. | desc. | % yield |
|---|---|---|---|---|---|---|---|---|---|---|
| 3 | O—CH₂—O | Me | ± | 65.91 / 66.11 | 6.55 / 6.28 | 5.91 / 5.92 | $C_{13}H_{15}NO_3 \cdot 0.2\, H_2O$ | — | oil | 61 |
| 4 | O—CH₂—O | Me | −31.5° | 66.42 / 66.45 | 6.52 / 6.70 | 5.96 / 5.86 | $C_{13}H_{15}NO_3 \cdot 0.1\, H_2O$ | 56–58 | white solid | 53 |
| 5 | O—CH₂—O | Et | ± | 68.00 / 67.78 | 6.93 / 6.69 | 5.66 / 5.56 | $C_{14}H_{17}NO_3$ | 84–86 | beige solid | 41 |
| 6 | O—CH₂—O | Et | −41.4° | 68.00 / 68.19 | 6.93 / 6.76 | 5.68 / 5.58 | $C_{14}H_{17}NO_3$ | 101–103 | white solid | 56 |
| 7 | O—CH₂—O | n-Pr | ± | 68.94 / 68.83 | 7.33 / 7.23 | 5.36 / 5.24 | $C_{15}H_{19}NO_3$ | 75–77 | waxy solid | 49 |
| 8 | O—CH₂—O | n-Pr | −32.6° | 68.94 / 68.66 | 7.33 / 7.32 | 5.36 / 5.52 | $C_{15}H_{19}NO_3$ | 82–84 | white solid | 58 |
| 9 | O—CH₂—O | c-Pr | ± | 69.48 / 69.22 | 6.61 / 6.78 | 5.40 / 5.31 | $C_{15}H_{17}NO_3$ | 127–129 | beige solid | 38 |
| 10 | O—CH₂—O | c-Pr | −32.6° | 69.00 / 68.69 | 6.64 / 6.56 | 5.36 / 5.42 | $C_{15}H_{17}NO_3 \cdot 0.1\, H_2O$ | 148–150 | white solid | 77 |
| 11 | O—CH₂—O | i-Pr | ± | 68.94 / 68.75 | 7.33 / 7.33 | 5.36 / 5.51 | $C_{15}H_{19}NO_3$ | 114–115 | solid | 50 |
| 12 | O—CH₂—O | i-Pr | − | 68.94 / 68.79 | 7.33 / 7.35 | 5.36 / 5.28 | $C_{15}H_{19}NO_3$ | 127–129 | beige solid | 54 |
| 13 | O—CH₂—O | NHEt | ± | 64.10 / 63.90 | 6.92 / 6.93 | 10.68 / 10.63 | $C_{14}H_{18}N_2O_3$ | 121–122 | white solid | 65 |
| 14 | O—CH₂—O | NHEt | −26.9° | 64.11 / 63.82 | 6.92 / 6.88 | 10.68 / 10.59 | $C_{14}H_{18}N_2O_3$ | 137–139 | white solid | 85 |
| 15 | O—(CH₂)₂—O | Me | ± | 65.60 / 65.75 | 6.66 / 6.45 | 5.35 / 5.27 | $C_{14}H_{17}NO_3 \cdot 0.15\, CH_2Cl_2$ | — | amber oil | 59 |
| 16 | O—(CH₂)₂—O | Et | ± | 67.36 / 67.47 | 7.14 / 7.21 | 5.17 / 5.18 | $C_{15}H_{19}NO_3 \cdot 0.1\, CH_2Cl_2$ | 67–69 | beige solid | 44 |
| 17 | O—(CH₂)₂—O | n-Pr | ± | 68.26 / 68.21 | 7.50 / 7.31 | 4.91 / 4.81 | $C_{16}H_{21}NO_3 \cdot 0.1\, CH_2Cl_2$ | — | amber oil | 49 |
| 18 | O—(CH₂)₂—O | c-Pr | ± | 70.31 / 69.89 | 7.01 / 6.74 | 5.12 / 5.10 | $C_{16}H_{19}NO_3$ | 96–98 | white solid | 68 |
| 19 | O—(CH₂)₂—O | i-Pr | ± | 69.01 / 68.88 | 7.59 / 7.71 | 5.00 / 4.95 | $C_{16}H_{21}NO_3 \cdot 0.05\, CH_2Cl_2$ | 100–102 | beige solid | 49 |
| 20 | O—(CH₂)₂—O | NHMe | ± | 63.23 / 63.42 | 6.98 / 7.31 | 10.54 / 10.59 | $C_{14}H_{18}N_2O_3 \cdot 0.2\, H_2O$ | 105–107 | white solid | 77 |
| 21 | O—(CH₂)₂—O | NHEt | ± | 65.20 / 64.92 | 7.29 / 7.41 | 10.14 / 10.01 | $C_{15}H_{20}N_2O_3$ | 92–94 | beige solid | 68 |
| 22 | CH=CH—O | Me | ± | 71.65 / 71.68 | 6.70 / 6.69 | 5.97 / 5.67 | $C_{14}H_{15}NO_1 \cdot 0.3\, H_2O$ | 88–89 | white solid | 31 |
| 23 | CH=CH—O | Et | ± | 74.04 / 73.80 | 7.04 / 6.96 | 5.76 / 5.70 | $C_{15}H_{17}NO_2$ | 84–85 | white solid | 57 |
| 24 | CH=CH—O | n-Pr | ± | 74.68 / 74.42 | 7.44 / 7.40 | 5.44 / 5.32 | $C_{16}H_{19}NO_2$ | 67–68 | white solid | 52 |
| 25 | CH=CH—O | c-Pr | ± | 73.71 / 73.45 | 6.81 / 6.81 | 5.37 / 5.12 | $C_{16}H_{17}NO_2 \cdot 0.3\, H_2O$ | 96–98 | beige solid | 63 |
| 26 | CH=CH—O | i-Pr | ± | 73.39 / 73.22 | 7.51 / 7.62 | 5.35 / 5.24 | $C_{16}H_{19}NO_2 \cdot 0.25\, H_2O$ | — | amber oil | 74 |

TABLE 2-continued

Physical Data for Compounds of Formula I

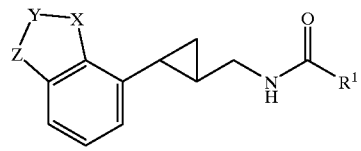

(I)

| Ex. | X—Y—Z | R¹ | $[\alpha]_D^{25}$ | % C Calc/Found | % H | % N | Emperical Formula | mp °C. | desc. | % yield |
|---|---|---|---|---|---|---|---|---|---|---|
| 27 | CH=CH—O | NHMe | ± | 67.15 / 66.97 | 6.43 / 6.58 | 11.03 / 10.74 | $C_{14}H_{16}N_2O_2 \cdot 0.1\ CH_2Cl_2$ | 97–98 | white solid | 58 |
| 28 | $CH_2$—$CH_2$—O | Me | ± | 71.04 / 70.79 | 7.50 / 7.41 | 5.92 / 5.58 | $C_{14}H_{17}NO_2 \cdot 0.3\ H_2O$ | — | oil | 54 |
| 29 | $CH_2$—$CH_2$—O | Et | ± | 72.11 / 72.09 | 7.87 / 7.96 | 5.61 / 5.44 | $C_{15}H_{19}NO_2 \cdot 0.25\ H_2O$ | — | oil | 64 |
| 30 | $CH_2$—$CH_2$—O | n-Pr | ± | 73.59 / 73.45 | 8.18 / 8.40 | 5.36 / 5.19 | $C_{16}H_{21}NO_2 \cdot 0.1\ H_2O$ | — | oil | 75 |
| 31 | CH=CH—O | cPr | −35.17 | 74.37 / 74.52 | 6.63 / 6.54 | 5.38 / 5.40 | $C_{16}H_{17}NO_2 \cdot 0.05\ C_4H_8O$ | 112–114 | beige solid | 54.7 |
| 32 | CH=CH—O | Et | −35.51 | 73.08 / 73.31 | 6.96 / 6.52 | 5.66 / 5.67 | $C_{15}H_{17}NO_2 \cdot 0.05\ CH_2Cl_2$ | 46–48 | tacky beige solid | 62.8 |
| 33 | $CH_2CH_2O$ | Et | 18.41 | 73.44 / 73.05 | 7.81 / 7.84 | 5.71 / 5.62 | $C_{15}H_{19}NO_2$ | 73.5–74 | white solid | 37.5 |
| 34 | $CH_2CH_2O$ | Me | — | 72.70 / 72.57 | 7.41 / 7.58 | 6.06 / 6.00 | $C_{14}H_{17}NO_2$ | 80–82 | off-white solid | 65.8 |
| 35 | $CH_2CH_2O$ | nPr | — | 71.61 / 72.01 | 8.26 / 8.39 | 5.22 / 4.77 | $C_{16}H_{21}NO_2 \cdot 0.5\ H_2O$ | — | amber oil | 95.0 |
| 36 | $CH_2CH_2O$ | NHMe | — | 67.77 / 67.54 | 7.39 / 7.55 | 11.29 / 11.41 | $C_{14}H_{18}N_2O_2 \cdot 0.10\ H_2O$ | 113–116 | off-white solid | 53.8 |
| 37 | $CH_2CH_2O$ | $CH_2OMe$ | — | 67.78 / 67.53 | 7.39 / 7.55 | 5.27 / 5.11 | $C_{15}H_{19}NO_3 \cdot 0.25\ H_2O$ | — | amber oil | 94.2 |
| 38 | $CH_2CH_2O$ | cPr | −8.38 | 74.16 / 73.93 | 7.47 / 7.39 | 5.41 / 5.38 | $C_{16}H_{19}NO_2 \cdot 0.10\ H_2O$ | 111–115 | off-white solid | 62.5 |
| 39 | $CH_2CH_2O$ | $CF_3$ | — | 58.95 / 58.83 | 4.95 / 4.94 | 4.91 / 4.76 | $C_{14}H_{14}F_3NO_2$ | 90–91 | white solid | 43.9 |
| 40 | $CH_2$—$(CH_2)_2$—O | Et | ± | 74.10 / 73.84 | 8.16 / 8.09 | 5.40 / 5.22 | $C_{16}H_{21}NO_2$ | 56–57 | white solid | 29 |
| 41 | $CH_2$—$(CH_2)_2$—O | cPr | ± | 75.25 / 74.98 | 7.80 / 7.75 | 5.16 / 5.01 | $C_{17}H_{21}NO_2$ | 132–134 | white solid | 40 |
| 42 | $CH_2$—$(CH_2)_2$—O | Et | −24.47 | 73.59 / 73.59 | 8.18 / 8.18 | 5.36 / 5.36 | $C_{16}H_{21}NO_2 \cdot 0.10\ H_2O$ | 83–84 | white solid | 32 |
| 43 | $CH_2$—$(CH_2)_2$—O | Me | −39.15 | 73.06 / 72.83 | 7.82 / 7.88 | 5.68 / 5.57 | $C_{15}H_{19}NO_2 \cdot 0.07\ H_2O$ | 131–132 | white solid | 13 |
| 44 | $CH_2$—$(CH_2)_2$—O | cPr | −35.28 | 74.75 / 74.42 | 7.82 / 7.68 | 5.13 / 5.04 | $C_{17}H_{21}NO_2 \cdot 0.10\ H_2O$ | 157–158 | white solid | 14 |
| 45 | O—$(CH_2)_2$—O | Et | −9.80 | 68.94 / 68.82 | 7.33 / 7.46 | 5.36 / 5.30 | $C_{15}H_{19}NO_3$ | 90–91 | white solid | 78.9 |
| 46 | O—$(CH_2)_2$—O | Me | — | 68.00 / 67.86 | 6.93 / 6.96 | 5.66 / 5.66 | $C_{14}H_{17}NO_3$ | 79–81 | beige solid | 82.9 |
| 47 | O—$(CH_2)_2$—O | NHMe | 3.71 | 63.24 / 63.37 | 6.97 / 7.29 | 10.53 / 10.41 | $C_{14}H_{18}N_2O_3 \cdot 0.2\ H_2O$ | 101–103 | off-white solid | 83.8 |
| 48 | O—$(CH_2)_2$—O | $CH_2OMe$ | 25.19 | 64.97 / 64.93 | 6.91 / 6.88 | 5.05 / 5.01 | $C_{15}H_{19}NO_4$ | 96–97 | off-white solid | 64.4 |
| 49 | O—$(CH_2)_2$—O | cPr | −10.51 | 70.31 / 70.29 | 7.01 / 7.02 | 5.12 / 5.08 | $C_{16}H_{19}NO_3$ | 122–123 | white solid | 75.4 |
| 50 | O—$(CH_2)_2$—O | nPr | −20.24 | 69.79 / 69.99 | 7.69 / 7.74 | 5.09 / 5.02 | $C_{16}H_{21}NO_3$ | 58–59 | off-white solid | 32.3 |
| 51 | O—$(CH_2)_2$—O | NHEt | 0.0 | 65.20 / 64.79 | 7.30 / 7.49 | 10.14 / 9.66 | $C_{15}H_{20}N_2O_3$ | 132–133 | off-white solid | 70.0 |
| 52 | O—$(CH_2)_2$—O | vinyl | 42.27 | 68.60 / 68.32 | 6.94 / 6.81 | 5.13 / 4.74 | $C_{15}H_{17}NO_3 \cdot 0.30\ C_2H_6O$ | — | amber oil | 84.7 |
| 53 | O—$(CH_2)_2$—O | iPr | −13.23 | 68.89 / 68.91 | 7.73 / 7.72 | 5.02 / 5.00 | $C_{16}H_2NO_3 \cdot 0.2\ H_2O$ | 123–124 | white solid | 54.7 |
| 54 | O—$(CH_2)_2$—O | $CF_3$ | — | 55.82 / 55.79 | 4.68 / 4.68 | 4.65 / 4.65 | $C_{14}H_{14}F_3NO_3$ | 119–121 | beige solid | 44.2 |
| 55 | O—$(CH_2)_2$—O | $CH_2CF_3$ | −12.22 | 57.14 / 57.01 | 5.12 / 5.07 | 4.44 / 4.43 | $C_{15}H_{16}F_3NO_3$ | 136.5–137.5 | off-white solid | 65.2 |
| 56 | O—$(CH_2)_2$—O | isopropenyl | — | 67.63 / 67.56 | 7.17 / 7.11 | 4.93 / 4.52 | $C_{16}H_{19}NO_3 \cdot 0.6\ H_2O$ | 144–150 | off-white solid | 42.7 |
| 57 | O—$(CH_2)_2$—O | Et | 2.63 | 68.94 / 68.58 | 7.33 / 7.38 | 5.36 / 5.02 | $C_{15}H_{19}NO_3$ | 77–78 | white solid | 13 |

TABLE 2-continued

Physical Data for Compounds of Formula I

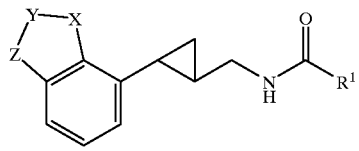

(I)

Elemental Analysis
Calculated over Found

| Ex. | X—Y—Z | R¹ | $[a]_D^{25}$ | % C | % H | % N | Emperical Formula | mp ° C. | desc. | % yield |
|---|---|---|---|---|---|---|---|---|---|---|
| 58 | O—(CH₂)₂—O | nPr | 3.07 | 69.79 | 7.69 | 5.09 | $C_{16}H_{21}NO_3$ | 40–41 | white solid | 14 |
|   |   |   |   | 69.58 | 7.89 | 5.12 |   |   |   |   |
| 59 | O—(CH₂)₃—O | Et | ± | 69.79 | 7.69 | 5.09 | $C_{16}H_{21}NO_3$ | 75–77 | white solid | 93.1 |
|   |   |   |   | 69.53 | 7.69 | 5.00 |   |   |   |   |
| 60 | O—(CH₂)₃—O | Me | ± | 68.94 | 7.33 | 5.36 | $C_{15}H_{19}NO_3$ | 73–75 | solid | 80.9 |
|   |   |   |   | 68.67 | 7.12 | 5.27 |   |   |   |   |
| 61 | CH₂—(CH₂)₃—O | Et | ± | 74.69 | 8.48 | 5.12 | $C_{17}H_{23}NO_2$ | 102.5–105 | white solid | 65.0 |
|   |   |   |   | 74.74 | 8.75 | 5.02 |   |   |   |   |
| 62 | CH₂—(CH₂)₃—O | nPr | ± | 75.22 | 8.77 | 4.87 | $C_{18}H_{25}NO_2$ | 95–97 | white solid | 84.5 |
|   |   |   |   | 75.36 | 9.06 | 4.77 |   |   |   |   |
| 63 | CH₂—(CH₂)₃—O | Me | ± | 74.10 | 8.16 | 5.40 | $C_{16}H_{21}NO_2$ | 70–72.5 | white solid | 61.0 |
|   |   |   |   | 73.82 | 8.08 | 5.27 |   |   |   |   |
| 64 | O—CH₂—CH₂ | Me | ± | 71.65 | 7.32 | 5.95 | $C_{14}H_{17}NO_2 \cdot 0.05\ CH_2Cl_2$ | 53–55 | white solid | 53 |
|   |   |   |   | 71.62 | 7.54 | 5.93 |   |   |   |   |
| 65 | O—CH₂—CH₂ | Et | ± | 73.44 | 7.81 | 5.71 | $C_{15}H_{19}NO_2$ | 90–92 | white solid | 72 |
|   |   |   |   | 73.20 | 7.49 | 5.63 |   |   |   |   |
| 66 | O—CH₂—CH₂ | nPr | ± | 74.10 | 8.16 | 5.40 | $C_{16}H_{21}NO_2$ | 88–90 | white solid | 50 |
|   |   |   |   | 73.91 | 8.14 | 5.40 |   |   |   |   |
| 67 | O—CH₂—CH₂ | cPr | ± | 74.68 | 7.44 | 5.44 | $C_{16}H_{19}NO_2$ | 125–127 | white solid | 88 |
|   |   |   |   | 74.42 | 7.41 | 5.31 |   |   |   |   |
| 68 | O—CH₂—CH₂ | NHMe | ± | 67.53 | 7.30 | 11.22 | $C_{14}H_{18}N_2O_2 \cdot 0.04\ CH_2Cl_2$ | 108–110 | yellow solid | 68 |
|   |   |   |   | 67.42 | 7.51 | 11.05 |   |   |   |   |
| 69 | CH₂—CMe₂O | Me | ± | 73.52 | 8.11 | 5.35 | $C_{16}H_{21}NO_2 \cdot 0.2\ CH_2Cl_2$ | — | clear oil | 68 |
|   |   |   |   | 73.45 | 8.09 | 5.34 |   |   |   |   |
| 70 | CH₂—CMe₂—O | Et | ± | 74.69 | 8.48 | 5.12 | $C_{17}H_{23}NO_2$ | 63–65 | white solid | 72 |
|   |   |   |   | 74.41 | 8.34 | 4.99 |   |   |   |   |
| 71 | CH₂—CMe₂O | nPr | ± | 75.22 | 8.77 | 4.87 | $C_{18}H_{25}NO_2$ | — | clear oil | 49 |
|   |   |   |   | 74.99 | 8.54 | 4.72 |   |   |   |   |
| 72 | CH₂—CMe₂O | iPr | ± | 75.22 | 8.77 | 4.87 | $C_{18}H_{25}NO_2$ | 110–112 | white solid | 65 |
|   |   |   |   | 75.35 | 8.66 | 4.76 |   |   |   |   |
| 73 | CH₂—CMe₂O | cPr | ± | 75.76 | 8.12 | 4.91 | $C_{18}H_{23}NO_2$ | 99–101 | white solid | 44 |
|   |   |   |   | 75.53 | 7.81 | 4.80 |   |   |   |   |
| 74 | CH=CMe—O | Me | ± | 74.05 | 7.04 | 5.76 | $C_{15}H_{17}NO_2$ | — | clear oil | 63 |
|   |   |   |   | 73.79 | 7.08 | 5.50 |   |   |   |   |
| 75 | CH=CMe—O | Et | ± | 73.89 | 7.38 | 5.37 | $C_{16}H_{19}NO_2 \cdot 0.4\ CH_2Cl_2$ | — | yellow oil | 72 |
|   |   |   |   | 73.61 | 7.38 | 5.09 |   |   |   |   |
| 76 | CH=CMe—O | nPr | ± | 75.25 | 7.80 | 5.16 | $C_{17}H_{21}NO_2$ | — | clear oil | 81 |
|   |   |   |   | 74.89 | 7.58 | 5.01 |   |   |   |   |
| 77 | O—CH=CH | Me | ± | 72.48 | 6.53 | 6.02 | $C_{17}H_{15}NO_2 \cdot 0.04\ CH_2Cl_2$ | — | clear oil | 58 |
|   |   |   |   | 72.32 | 6.64 | 5.94 |   |   |   |   |
| 78 | O—CH=CH | Et | ± | 72.82 | 6.95 | 5.64 | $C_{15}H_{17}NO_2 \cdot 0.6\ CH_2Cl_2$ | 53–55 | white powder | 49 |
|   |   |   |   | 72.82 | 7.08 | 5.42 |   |   |   |   |
| 79 | O—CH=CH | nPr | ± | 74.68 | 7.44 | 5.44 | $C_{16}H_{19}NO_2$ | — | clear oil | 51 |
|   |   |   |   | 74.31 | 7.53 | 5.22 |   |   |   |   |
| 80 | O—CH=CH | cPr | ± | 75.27 | 6.71 | 5.49 | $C_{16}H_{17}NO_2$ | 110–112 | white solid | 58 |
|   |   |   |   | 74.99 | 6.76 | 5.21 |   |   |   |   |
| 81 | CH₂(CHMe)O | Me | 9.5 | 72.12 | 7.87 | 5.61 | $C_{15}H_{19}NO_2/0.25\ H_2O$ | — | oil | 70 |
|   |   |   |   | 72.29 | 8.24 | 5.37 |   |   |   |   |
| 82 | CH₂(CHMe)O | Et | 15 | 74.10 | 8.16 | 5.40 | $C_{16}H_{21}NO_2$ | 85–86 | white solid | 70 |
|   |   |   |   | 73.75 | 8.31 | 5.24 |   |   |   |   |
| 83 | CH₂(CHMe)O | nPr | 14.3 | 74.69 | 8.48 | 5.12 | $C_{17}H_{23}NO_2$ | 62.5–63.5 | white solid | 65 |
|   |   |   |   | 74.62 | 8.48 | 5.04 |   |   |   |   |
| 84 | CH₂(CHMe)O | cPr | 13.39 | 75.25 | 7.80 | 5.16 | $C_{17}H_{21}NO_2$ | 126–127 | white solid | 73 |
|   |   |   |   | 74.89 | 7.81 | 4.89 |   |   |   |   |
| 85 | CH₂(CHMe)O | NHEt | 30.5 | 70.04 | 8.08 | 10.21 | $C_{16}H_{22}N_2O_2$ | 118–119 | white solid | 65 |
|   |   |   |   | 69.80 | 8.11 | 9.95 |   |   |   |   |
| 86 | CH₂(CHMe)O | iPr | 12.7 | 74.69 | 8.48 | 5.12 | $C_{17}H_{23}NO_2$ | 104.5–105.5 | white solid | 60 |
|   |   |   |   | 74.63 | 8.38 | 5.01 |   |   |   |   |
| 87 | CH₂(CHMe)O | CH₂Cl | 22.7 | 64.40 | 6.49 | 5.01 | $C_{15}H_{18}ClNO_2$ | 73.5–74.5 | white solid | 70 |
|   |   |   |   | 64.15 | 6.50 | 4.82 |   |   |   |   |
| 88 | CH₂(CHMe)O | Et | −48.6 | 72.10 | 8.24 | 5.25 | $C_{16}H_{21}NO_2/0.4\ H_2O$ | 98–99 | white solid | 71 |
|   |   |   |   | 71.94 | 8.19 | 5.43 |   |   |   |   |

TABLE 2-continued

Physical Data for Compounds of Formula I

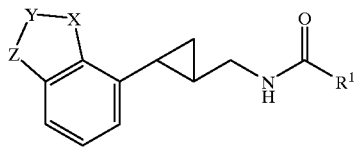

(I)

Elemental Analysis
Calculated over Found

| Ex. | X—Y—Z | R[1] | $[a]_D^{25}$ | % C | % H | % N | Emperical Formula | mp ° C. | desc. | % yield |
|---|---|---|---|---|---|---|---|---|---|---|
| 89 | CH$_2$(CHMe)O | iPr | −49.2 | 73.24 | 8.53 | 5.02 | C$_{17}$H$_{23}$NO$_2$/0.3 H$_2$O | 106–107 | white solid | 72 |
|  |  |  |  | 73.22 | 8.37 | 5.06 |  |  |  |  |
| 90 | CH$_2$(CHMe)O | Me | −55.7 | 73.44 | 7.81 | 5.71 | C$_{15}$H$_{19}$NO$_2$ | 117–118 | white solid | 67 |
|  |  |  |  | 73.42 | 7.90 | 5.65 |  |  |  |  |
| 91 | CH$_2$(CHMe)O | CH$_2$OMe | −31 | 69.79 | 7.69 | 5.09 | C$_{16}$H$_{21}$NO$_3$ | 75–76 | white solid | 61 |
|  |  |  |  | 69.86 | 7.82 | 5.05 |  |  |  |  |
| 92 | CH$_2$(CHMe)O | cPr | −48.6 | 75.25 | 7.80 | 5.16 | C$_{17}$H$_{21}$NO$_2$ | 120–121 | white solid | 75 |
|  |  |  |  | 75.13 | 7.87 | 5.08 |  |  |  |  |
| 93 | CH$_2$(CHMe)O | NHEt | −25.53 | 70.04 | 8.08 | 10.21 | C$_{16}$H$_{22}$N$_2$O$_2$ | 115–116 | white solid | 61 |
|  |  |  |  | 69.83 | 8.10 | 10.09 |  |  |  |  |
| 94 | CH$_2$(CHMe)O | nPr | −45.6 | 74.69 | 8.48 | 5.12 | C$_{17}$H$_{23}$NO$_2$ | 74–75 | white solid | 69 |
|  |  |  |  | 74.46 | 8.34 | 4.83 |  |  |  |  |

Example 95

N-[[2-(2-Methyl-4-benzofuranyl)-3,3-difluorocyclopropanyl]-methyl]propanamide

Obtained 95% of a white solid. m.p. 55–56° C.
Anal. Calc'd for C$_{16}$H$_{17}$F$_2$NO$_2$: C, 65.52; H, 5.84; N, 4.78. Found: C, 66.15; H, 5.95; N, 4.73.

Example 96

(+)-(trans)-N-[[2-(3,4-dihydro-2H-1-benzopyran-5-yl)cycloprop-1-yl]methyl]propanamide Obtained 14% of a white solid. m.p. 81–82° C. $[\alpha]_D^{25}$= 16.29. Purity=95% by HPLC. $^1$H NMR (300 MHz, CDCl$_3$) δ 6.98 (t, J=7.8 Hz, 1H), 6.65 (d, J=7.9 Hz, 1H), 6.50 (d, J=7.5 Hz, 1H), 5.57 (s, 1H), 4.13 (t, J=4.5 Hz, 2H), 3.49-3.30 (m,1H), 3.23-3.16 (m,1H), 2.84-2.78 (m, 2H), 2.21 (q, J=7.6 Hz, 2H), 2.07-1.99 (m, 2H), 1.75-1.69 (m,1 H), 1.26-1.09 (m, 4H), 0.92-0.81 (m, 2H); $^{13}$C NMR (75 MHz, CDCl$_3$) δ 173.9, 155.2, 141.1, 126.1, 117.6, 115.1, 66.0, 43.9, 30.0, 22.6, 20.9, 19.6, 12.7, 10.1.

Example 97

(±)-(trans)-N-[[2(3,4-dihydro-2H-1-benzopyran-5-yl)cycloprop-1-yl]methyl]butanamide Obtained 10% of a yellow oil. Purity=87% by NMR.$^1$H NMR (300 MHz, CDCl$_3$) δ 6.95 (d, J=7.8 Hz, 1H), 6.60 (d, J=7.4 Hz,1H), 6.50 (d, J=7.9 Hz,1H), 5.58 (s,1H), 4.07 (t, J=4.7 Hz, 2H), 3.44-3.35 (m,1H), 3.25-3.11 (m, 1H), 2.78-2.73 (m, 2H), 2.13-2.08 (t, J=7.3 Hz, 2H), 2.02-1.94 (m, 2H), 1.70-1.55 (m, 3H), 1.23-1.09 (m, 1H), 0.91-0.75 (m, 5H); $^{13}$C NMR (75 MHz, CDCl$_3$) δ155.1, 141.0, 126.8, 122.1, 117.5, 115.1, 65.9, 43.8, 38.9, 22.5, 20.8, 19.5, 19.3, 13.9, 12.7.

Example 98

(+)-(trans)-N-[[2-(2,3-Dihydro-1,4-benzodioxin-5-yl)cycloprop-1-yl]methyl]acetamide Obtained 18% of an oil. $[\alpha]_D^{25}$=5.89. Purity =99% by HPLC. $^1$H NMR (300 MHz, CDCl$_3$) δ 6.77-6.71 (m, 2H), 6.50-6.44 (m, 1H), 6.04 (s, 1H), 4.36-4.33 (m, 2H), 4.29-4.26 (m, 2H), 3.70-3.62 (m, 1H), 2.87-2.79 (m, 1H), 1.99 (s, 3H), 1.86-1.80 (m, 1H), 1.15-1.00 (m, 2H), 0.87-0.81 (m, 1H); $^{13}$C NMR (75 MHz, CDCl$_3$) δ143.3, 130.4, 120.9, 118.5, 115.4, 64.6, 64.1, 44.3, 23.4, 20.8, 16.3, 11.8.

Example 99

N-[[2-(2-Methyl-4-benzofuranyl)-3,3-difluorocyclopropanyl]-methyl]acetamide

Obtained 90% of a colorless liquid. Purity=98% by HPLC. $^1$H NMR (300 MHz, CDCl$_3$) δ 2.01 (s, 3H), 2.17–2.29 (m, 1H), 2.45 (s, 3H), 2.70 (m, 1H), 3.29 (m,1H), 3.92 (m, 1H), 5.89 (bs,1H), 6.44 (s, 1H), 6.97 (d, J=7.5 Hz, 1H), 7.13 (t, J=7.5 Hz, 1H), 7.31 (d, J=7.5 Hz, 1H). $^{13}$C NMR (75 MHz, CDCl$_3$) δ 14.2, 23.3, 28.4 (t, J=10.0 Hz), 29.7 (t, J=10.0 Hz), 37.3, 101.7, 110.2, 114.0 (t, J=288 Hz), 121.3, 123.1, 124.4, 129.5, 154.6, 156.0, 170.4.

Example 100

(trans)-N-Methyl-N-[[2-(2,3-dihydrobenzofuran-4-yl)cyclopropyl]methyl]propanamide To a solution of (trans)-N-[[2-(2,3-dihydrobenzofuran-4-yl)cyclopropyl]methyl]propanamide (120 mg, 0.6 mmol) in THF (1.5 mL) was added sodium hydride (30 mg of 60%, 0.75 mmol). The mixture was allowed to stir for 0.5 h and iodomethane (140 mg, 1 mmol) was added. After stirring for 18 h, the solution was concentrated in vacuo. The residue was dissolved in acetonitrile and washed with hexane. The acetonitrile solution was concentrated in vacuo and the residue purified by chromatography on silica eluting with ethyl acetate-hexane (2:8) to give the product as an amber oil (90 mg, 69%).
Anal. Calc'd for C$_{16}$H$_{21}$NO$_2$•0.2H$_2$O: C, 73.08; H, 8.20; N 5.33. Found: C, 72.91; H, 8.24; N, 5.23.

Example 101

(trans)-N-[[2-(2,3-Dihydro-5,7-diiodobenzofuran-4-yl)cyclopropyl]methyl]propanamide To a solution of (trans)-N-[[2-(2,3-dihydrobenzofuran-4-yl)cyclopropyl]methyl]propanamide (0.245 mg, 1 mmol)

and lead IV tetraacetate (530 mg, 1.2 mmol) in 1.5 mL acetic acid was added iodine (300 mg, 1.2 mmol). The solution was allowed to stir for 15 min during which time the reaction solidified. The mixture was diluted with methylene chloride and the resulting solution was washed with water and saturated sodium bicarbonate solution and dried. The solution was concentrated in vacuo and the residue crystallized form isopropyl ether to give the product (500 mg, 99%, MP 198–199° C.).

Anal. Calc'd for $C_{15}H_{17}I_2NO_2$: C, 36.24; H, 3.45; N 2.82. Found: C, 36.29; H, 3.59; N, 2.96.

Example 102

(trans)-N-[[2-(2,3-Dihydro-5-iodobenzofuran-4-yl) cyclopropyl]methyl]propanamide To a solution of 0.12 g (0.6 mmol) (trans)-N-[[2-(2,3-dihydrobenzofuran-4-yl)cyclopropyl]methyl]propanamide and 0.27 g (0.6 mmol) of lead IV tetraacetate in 1 mL acetic acid was added 0.075 g (0.25 mmol) iodine. The solution was allowed to stir for 1.5 h and was diluted with methylene chloride. The resulting solution was washed with water and saturated sodium bicarbonate solution and dried. The solution was concentrated in vacuo and the residue purified by chromatography on silica eluting with ethyl acetate-hexane, 3:7 containing 0.2% methanol to give the product (25 mg, 11%, mp 148–149° C.).

Anal. Calc'd for $C_{15}H_{18}INO_2 \cdot 0.1H_2O$: C, 48.30; H, 4.92; N 3.75. Found: C, 47.94; H, 4.67; N, 3.70.

Reasonable variations, such as those which would occur to a skilled artisan, can be made herein without departing from the scope of the invention.

We claim:

1. A compound of Formula I or a pharmaceutically acceptable solvate thereof having the Formula:

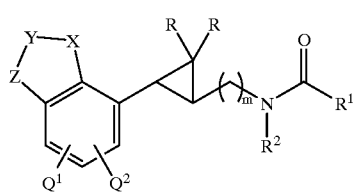

(I)

wherein $Q^1$ and $Q^2$ each are independently hydrogen or halogen;

X is oxygen;

Y is $(CH_2)_n$, with n=1–4;

Z is oxygen;

R is hydrogen, halogen or $C_{1-4}$ alkyl in both cases;

m is 1 or 2;

$R^1$ is $C_{1-6}$ alkyl, $C_{3-6}$ cycloalkyl, $C_{1-3}$ haloalkyl, $C_{1-6}$ alkylamino, $C_{2-6}$ alkenyl, $C_{1-4}$ alkoxy($C_{1-4}$)alkyl, $C_{1-4}$ alkylthio($C_{1-4}$)alkyl or $C_{1-4}$ trifluoromethylalkyl; and $R^2$ is hydrogen or $C_{1-4}$ alkyl.

2. The compound of claim 1 wherein $Q^1$ and $Q^2$ are independently hydrogen or iodo and m is 1.

3. The compound of claim 2 wherein $R^1$ is $C_{1-6}$ alkyl, $C_{3-4}$ cycloalkyl, $C_{1-3}$ haloalkyl, $C_{2-3}$ alkenyl, $C_{1-2}$ alkoxy($C_{1-2}$) alkyl or $C_{1-2}$ trifluoromethylalkyl and $R^2$ is hydrogen.

4. The compound of claim 3 wherein X is oxygen, Y is $(CH_2)_n$ in which n is 1 or 2 and Z is oxygen.

5. The compound of claim 4, selected from the group consisting of:

(trans)-N-[[2-(1,3-benzodioxol-4-yl)cycloprop-1-yl] methyl]acetamide;

(−)-(trans)-N-[[2-(1,3-benzodioxol-4-yl)cycloprop-1-yl] methyl]acetamide;

(trans)-N-[[2-(1,3-benzodioxol-4-yl)cycloprop-1-yl] methyl]propanamide;

(−)-(trans)-N-[[2-(1,3-benzodioxol-4-yl)cycloprop-1-yl] methyl] propanamide;

(trans)-N-[[2-(1,3-benzodioxol-4-yl)cycloprop-1-yl] methyl]butanamide;

(−)-(trans)-N-[[2-(1,3-benzodioxol-4-yl)cycloprop-1-yl] methyl] butanamide;

(trans)-N-[[2-(1,3-benzodioxol-4-yl)cycloprop-1-yl] methyl]cyclopropane carboxamide;

(−)-(trans)-N-[[2-(1,3-benzodioxol-4-yl)cycloprop-1-yl] methyl] cyclopropane carboxamide;

(trans)-N-[[2-(1,3-benzodioxol-4-yl)cycloprop-1-yl] methyl]-2-methylpropanamide;

(−)-(trans)-N-[2-(1,3-benzodioxol-4-yl)cycloprop-1-yl] methyl]-2-methylpropanamide;

(−)-(trans)-N-[[2-(2,3-dihydro-1,4-benzodioxin-5-yl) cycloprop-1-yl]methyl]propanamide;

(−)-(trans)-N-[[2-(2,3-dihydro-1,4-benzodioxin-5-yl) cycloprop-1-yl]methyl]acetamide;

(−)-(trans)-N-[[2-(2,3-dihydro-1,4-benzodioxin-5-yl) cycloprop-1-yl]methyl]cyclopropanecarboxamide;

(−)-(trans)-N-[[2-(2,3-dihydro-1,4-benzodioxin-5-yl) cycloprop-1-yl]methyl]butanamide;

(+)-(trans)-N-[[2-(2,3-dihydro-1,4-benzodioxin-5-yl) cycloprop-1-yl]methyl]propenamide;

(−)-(trans)-N-[[2-(2,3-dihydro-1,4-benzodioxin-5-yl) cycloprop-1-yl]methyl]trifluoroacetamide;

(−)-(trans)-N-[[2-(2,3-dihydro-1,4-benzodioxin-5-yl) cycloprop-1-yl]methyl]-3,3,3-trifluoropropanamide;

(+)-(trans)-N-[[2-(2,3-dihydro-1,4-benzodioxin-5-yl) cycloprop-1-yl]methyl]propanamide;

(trans)-N-[[2-(2,3-dihydro-1,4-benzodioxin-5-yl) cycloprop-1-yl]-methyl]acetamide;

(trans)-N-[[2-(2,3-dihydro-1,4-benzodioxin-5-yl) cycloprop-1-yl]-methyl]propanamide;

(trans)-N-[[2-(2,3-dihydro-1,4-benzodioxin-5-yl) cycloprop-1-yl]-methyl]butanamide;

(trans)-N-[[2-(2,3-dihydro-1,4-benzodioxin-5-yl) cycloprop-1-yl]methyl]-2-methylpropanamide; and (trans)-N-[[2-(2,3-dihydro-1,4-benzodioxin-5-yl) cycloprop-1-yl]-methyl]cyclopropane carboxamide.

6. The compound of claim 5, selected from the group consisting of:

(trans)-N-[[2-(1,3-benzodioxol-4-yl)cycloprop-1-yl] methyl]acetamide;

(−)-(trans)-N-[[2-(1,3-benzodioxol-4-yl)cycloprop-1-yl] methyl]acetamide;

(trans)-N-[[2-(1,3-benzodioxol-4-yl)cycloprop-1-yl] methyl]propanamide;

and (−)-(trans)-N-[[2-(1,3-benzodioxol-4-yl)cycloprop-1-yl]methyl] propanamide.

7. The compound of claim 5, selected from the group consisting of:

(−)-(trans)-N-[[2-(2,3-dihydro-1,4-benzodioxin-5-yl) cycloprop-1-yl]methyl]propanamide;

(−)-(trans)-N-[[2-(2,3-dihydro-1,4-benzodioxin-5-yl) cycloprop-1-yl]methyl]acetamide;

(−)-(trans)-N-[[2-(2,3-dihydro-1,4-benzodioxin-5-yl)cycloprop-1-yl]methyl]cyclopropanecarboxamide; and (−)-(trans)-N-[[2-(2,3-dihydro-1,4-benzodioxin-5-yl)cycloprop-1-yl]methyl]butanamide.

8. A method of treating sleep disorders in a patient in need of such treatment comprising administering to said patient a therapeutic amount of a compound of claim 1.

9. A composition useful for treating sleep disorders comprising a therapeutic amount of a compound of claim 1 and a suitable amount of a pharmaceutically acceptable carrier.

10. A method of treating circadian rhythm-related disorders in a patient in need of such treatment comprising administering to said patient a therapeutic amount of a compound of claim 1.

11. A composition useful for treating circadian rhythm-related disorders comprising a therapeutic amount of a compound of claim 1 and a suitable amount of a pharmaceutically acceptable carrier.

* * * * *